(12) United States Patent
Hunn et al.

(10) Patent No.: US 8,801,660 B2
(45) Date of Patent: *Aug. 12, 2014

(54) INFUSION SET

(71) Applicant: Roche Diagnostic International AG, Rotkreuz (CH)

(72) Inventors: Marcel Hunn, Langenthal (CH); Juerg Liniger, Ostermundigen (CH); Patrik Denoth, Muechenwiler (CH); Marc Oesch, Krauchthal (CH); Markus Buetikofer, Wattenwil (CH); Rudolf Zihlmann, Langnau (CH); Simon Scheurer, Bern (CH)

(73) Assignee: Roche Diagnostics International AG, Rotkreuz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/925,183

(22) Filed: Jun. 24, 2013

(65) Prior Publication Data
US 2013/0281931 A1 Oct. 24, 2013

Related U.S. Application Data

(60) Continuation of application No. 12/971,986, filed on Dec. 17, 2010, now Pat. No. 8,469,929, which is a division of application No. 10/679,925, filed on Oct. 6, 2003, now Pat. No. 7,879,010, which is a continuation of application No. PCT/CH02/00186, filed on Apr. 3, 2002.

(30) Foreign Application Priority Data

Apr. 6, 2001 (DE) .................................. 10 117 285
Jun. 19, 2001 (DE) .............................. 20 110 059 U

(51) Int. Cl.
*A61M 31/00* (2006.01)
*A61M 37/00* (2006.01)

(52) U.S. Cl.
USPC .............. 604/93.01; 604/164.01; 604/164.04; 604/180; 604/244

(58) Field of Classification Search
USPC ......... 604/164.01, 174, 180, 244, 533, 93.01, 604/164.04
See application file for complete search history.

(56) References Cited

U.S. PATENT DOCUMENTS

| | | |
|---|---|---|
| 3,797,489 A | 3/1974 | Sarnoff |
| 4,994,042 A | 2/1991 | Vadher |
| 5,129,884 A | 7/1992 | Dysarz |
| 5,292,310 A | 3/1994 | Yoon |
| 5,540,664 A | 7/1996 | Wyrick |
| 5,545,143 A | 8/1996 | Fischell |
| 5,573,510 A | 11/1996 | Isaacson |

(Continued)

FOREIGN PATENT DOCUMENTS

| | | |
|---|---|---|
| DE | 4013769 A1 | 10/1991 |
| DE | 9200192 U1 | 3/1992 |

(Continued)

*Primary Examiner* — Theodore Stigell
(74) *Attorney, Agent, or Firm* — Dinsmore & Shohl LLP

(57) ABSTRACT

A device for inserting a cannula into tissue, including a cannula, a protective element which can accommodate said cannula, an operating element for moving the cannula out of the protective element, and a holder fixedly connected to the cannula. The invention encompasses a system for connecting a liquid supply to the cannula.

23 Claims, 18 Drawing Sheets

(56) References Cited

U.S. PATENT DOCUMENTS

| | | | |
|---|---|---|---|
| 5,762,630 A | 6/1998 | Bley et al. | |
| 6,093,172 A | 7/2000 | Funderburk et al. | |
| 7,022,108 B2 | 4/2006 | Marano-Ford et al. | |
| 7,879,010 B2 * | 2/2011 | Hunn et al. | 604/164.12 |
| 8,469,929 B2 * | 6/2013 | Hunn et al. | 604/164.01 |
| 2001/0023889 A1 | 9/2001 | Bendall et al. | |
| 2002/0022855 A1 | 2/2002 | Bobroff et al. | |

FOREIGN PATENT DOCUMENTS

| | | | |
|---|---|---|---|
| DE | 69603379 | T2 | 8/1996 |
| DE | 19631921 | A1 | 3/1997 |
| DE | 69606993 | T2 | 3/1998 |
| DE | 29905066 | U1 | 9/1999 |
| DE | 29905069 | U1 | 9/1999 |
| DE | 19912459 | A1 | 9/2000 |
| DE | 10008825 | A1 | 9/2001 |
| EP | 0290176 | | 4/1987 |
| EP | 0451040 | | 10/1991 |
| EP | 0615768 | | 9/1994 |
| EP | 0645159 | A1 | 3/1995 |
| EP | 0956879 | A1 | 11/1999 |
| FR | 2781378 | A1 | 1/2000 |
| WO | 9933504 | A1 | 7/1999 |
| WO | 0003757 | A1 | 1/2000 |
| WO | 0137915 | A2 | 5/2001 |

* cited by examiner

INFUSION SET

CROSS-REFERENCE TO RELATED APPLICATIONS

This application is a Continuation of U.S. patent application Ser. No. 12/971,986, filed Dec. 17, 2010, now U.S. Pat. No. 8,469,929, which is a Divisional of U.S. patent application Ser. No. 10/679,925, filed Oct. 6, 2003, now U.S. Pat. No. 7,879,010, which is a continuation of International Patent Application PCT/CH02/00186, filed on Apr. 3, 2002, which claims priority to German Application No. 101 17 285.0, filed on Apr. 6, 2001 and German Application No. 201 10 059.2, filed on Jun. 19, 2001, the contents of each of which are hereby incorporated in their entirety by reference herein.

BACKGROUND OF THE INVENTION

The present invention relates to an infusion set, in particular to a device for inserting a cannula into tissue, for example skin tissue, fatty tissue or muscle tissue, and to a device for supplying a liquid via the cannula into the tissue.

A device for inserting a catheter comprising a needle is known from EP 0 451 040 A1, wherein a cover is provided which may be pushed together over the needle. The catheter can thus be inadvertently removed even by small drag forces acting on the catheter, and lies open, relatively unprotected, at the injection point; see FIG. 1 in EP 0 451 040 A1.

EP 0 290 176 A1 discloses a device for inserting a cannula comprising a needle, wherein the needle has to be pressed against a spring when being inserted and is retracted by the spring force into a casing after the insertion process. Here, too, the cannula is relatively unprotected once inserted, and can easily be inadvertently removed.

A device for subcutaneously supplying a medicine is known from EP 0 615 768 B1. A cannula comprising a needle is inserted, wherein at the same time as the cannula is inserted, an arrangement connected fixedly to the cannula and having an adhesive underside is applied to the skin, which makes the injection process, which is often unpleasant for the user, additionally difficult.

In the known devices, the cannula is either relatively unprotected against being unintentionally removed, a drag force acts on the cannula inserted into the tissue even as the needle is removed from the cannula, or an additional device has to be moved together with the cannula during the injection process, which makes positioning it exactly difficult.

BRIEF SUMMARY OF THE INVENTION

It is an object of the present invention to provide a device which improves the insertion of a cannula. In general terms, an infusion set is provided which exhibits improvements with respect to the prior art.

A device in accordance with the invention for inserting a cannula into a tissue, in some embodiments preferably for subcutaneously or transcutaneously administering a liquid, comprises a cannula which, in one embodiment, is formed as a hard cannula, such that it can be inserted into the tissue without an additional needle or other injection element, e.g., by absorbing liquid, wherein the cannula is preferably elastic or flexible once it has been inserted into the tissue. It is, however, also possible to provide a known cannula which is inserted into the tissue in a known way, using, for example, a guiding needle or other injection element. Furthermore, a protective element is provided which can accommodate the cannula before it is inserted into the tissue, wherein the protective element is preferably formed such that the tip of the cannula, or also of a needle suitable for inserting the cannula, which penetrates into the tissue is covered by the protective element such that a user cannot inadvertently come into contact with said tip and be injured by said tip.

In some embodiments, the protective element can surround the tip of the cannula partially or completely or can surround the entire cannula, or a needle provided for inserting the cannula as the case may be, in order to guarantee the protective function. Furthermore, an operating element is provided whereby the cannula or needle and cannula can be moved out of the protective element, in order to insert the cannula into the tissue. In some embodiments, if a needle is used, it is preferable if, once the cannula has been inserted, the needle can be moved back into the protective element again, using the operating element or also automatically, e.g., using a spring mechanism, in order to also minimize or rule out the danger of injury once the cannula has been inserted.

In some embodiments, in accordance with the invention, the cannula is connected to a holder which can be provided at the distal end, i.e., the end facing away from the tip of the cannula. In some embodiments, the holder can be moved with the cannula and, when inserting the cannula, can fix the cannula in a fixed position, for example by latching—or more generally, connecting—said holder to a foundation body, already fixedly arranged over the injection point before the cannula is injected. If, for example, a needle is removed from a cannula after said cannula has been inserted, then it is possible due to the holder connected to the cannula to ensure that when a holding force is applied to the holder, e.g., by connecting the holder to a foundation body, the removing force of the needle does not act directly on the cannula, i.e., the cannula is not strained in the extraction direction when it is extracted.

In accordance with the invention, it is possible to relieve the cannula when extracting a needle by suitably holding and/or fastening the holder, and to secure the cannula against being unintentionally removed. If a cannula is inserted without using a needle, then the holder in accordance with the invention exhibits the advantage that the inserted cannula can be secured against being unintentionally removed, by the holder and as the case may be by an element connected to the holder. Using the device in accordance with the invention, the injection process may be simply and relatively safely performed.

Although this description talks of "expelling" a needle or cannula using an "expelling element," it should be noted that this is also intended to mean removing using a drag element, i.e., a movement can be caused by a drag and/or pressure force or a drag or pressure spring.

The holder connected to the cannula is advantageously formed such that it can establish a connection with another element, preferably a base body which may be adhered to the skin above an injection point, said base body advantageously being arranged such that it connects with the holder when the cannula is completely or almost completely expelled. This connection can be a latch connection, wherein one or more grooves or recesses and/or projections or latching edges can be provided on the holder, enabling a detachable or non-detachable fixed connection between the holder and a suitable element. Other suitable connections or connective structures may be used as well.

In a preferred embodiment, a needle is provided which the cannula can be inserted into a tissue, wherein the needle is advantageously surrounded by the cannula. It is particularly advantageous to design the device such that, once the cannula has been inserted, the needle can be re-inserted, in some embodiments preferably completely, back into the protective element, e.g., by a movement of an operating element and/or a spring which is compressed when the cannula is inserted into the tissue and the needle is extended out of the protective element and generates a force which moves the needle back to its initial position in the protective element.

In some embodiments, the device is preferably designed such that it can be fixedly or detachably connected to a base body and, particularly advantageously, is already connected to the base body in an initial state, such that application or use is simplified for the user. The base body can consist of a plaster which may be adhered to a point on the skin and a foundation body arranged on said plaster, on which foundation body the device for inserting the cannula is arranged. In such a configuration, the tip of the cannula or needle can be arranged actually relatively near to an exit opening of the base body, such that once the plaster has been adhered to an area of skin, the cannula or needle can be immediately inserted into the skin. The tip of the cannula or needle can also protrude out of the protective element without there being a danger of injury for a user, since the tip is shielded by the surrounding base body. Advantageously, the passage opening provided in the base body for the tip of the cannula or needle is relatively small, preferably only slightly larger than the diameter of the cannula, in order to rule out the possibility of the user reaching through the passage opening, thus minimizing the danger of injury. Once the cannula has been inserted, and the needle retracted into the protective element, the device can be detached again from the base body, such that a fluid supply can be connected to the cannula.

In some preferred embodiments, the device for inserting the cannula can be connected to the base body, particularly to the foundation body via a connecting element, such as a latch connection which preferably can also be detached.

In a preferred embodiment of the invention, the protective element is a frame which at least partially surrounds the cannula or needle when they are retracted. In one embodiment, the protective element is a sheath which completely surrounds the cannula or needle when they are retracted, wherein a passage opening is provided in the protective element, through which the cannula or needle can be moved out of the protective element and/or inserted back into the protective element. Said passage opening can be open and slightly larger than the outer diameter of the cannula. It is also possible to seal the passage opening using a suitable covering element which can be moved away from the passage opening when the cannula or needle is extended or which is formed elastically such that the cannula or needle can pierce it.

The device is advantageously designed such that the operating element, or also a needle element provided for inserting the cannula, can—when retracted and once the cannula has been inserted—be connected, in particular latched, to the protective element, such that the needle is prevented from being inadvertently re-expelled from the protective element and the possibility of a user being unintentionally injured is thus ruled out.

In one preferred embodiment, the device—in particular the operating element—is formed such that when the cannula is expelled, the device for inserting the cannula can be prevented from being detached from a base body connected to the device. To this end, a transverse element which is connected to the operating element and may be shifted can be provided, the transverse element preventing holding elements provided for connecting to the base body from being pressed together when the cannula is expelled, thus enabling the possibility of loosening the device from the base body, which can only be achieved by pressing said holding elements together, to be ruled out. In general terms, any arrangement or element can be used which is able to offer such a securing function. This can ensure that the cannula inserting device is not inadvertently detached from the base body, when for example a needle is extended out of the protective element, which could lead to a user being injured.

In some embodiments, a sealing element or septum is preferably provided in the holder, for sealing the upper side of the cannula or a liquid space, wherein said sealing element or septum can be penetrated by a needle and/or a liquid supply and can guarantee a liquid-proof connection. If an element is not inserted into the septum, then it can completely seal the access to the cannula or a liquid space lying above the cannula. Suitable materials for this are known in the prior art.

In accordance with another aspect of the invention, a base body is provided which consists of a plaster which may be adhered to a point on the skin and a foundation body arranged on said plaster, wherein the base body or foundation body comprises at least one detachable connecting element to which the device described above for inserting a cannula can be attached and to which a device for supplying a fluid or liquid can be attached, such that when the base body is attached above an insertion point of the cannula, both the device for inserting the cannula and a device for supplying a fluid can be attached, together or in succession, to the same or to different connecting elements on the base body. In some preferred embodiments, the device for inserting the cannula can already be fixedly and detachably connected to the base body in its initial state, such that the base body together with the inserting device for the cannula can be attached above an insertion point of the cannula, wherein once the cannula has been inserted, the inserting device can be detached again from the base body. It is possible to connect to the base body to the cannula inserting device just before inserting the cannula.

The at least one connecting element provided on the base body advantageously serves both to connect to the inserting device for the cannula and to connect to the device for supplying a fluid, such that once the inserting device for the cannula has been detached, the device for supplying the fluid can be attached to the same connecting element(s) which previously served to fasten the inserting device for the cannula.

In some embodiments, the at least one connecting element provided on the base body is preferably an element which enables a latch connection, i.e., in particular a groove and/or latching edge or latching projection using which a latch connection with the inserting device for the cannula and/or the fluid supplying device can be established.

In accordance with another aspect of the present invention, a system is proposed using which a liquid supply can be connected to a cannula, wherein a foundation body is provided which comprises a cannula which is already inserted into a tissue, e.g., using the device described above. The foundation body has at least one opening which is connected to the cannula or the hollow space of the cannula. For supplying the liquid, a plug comprising a supplying element is provided which can be inserted into the opening of the foundation body, such that the liquid can be channeled via the supplying element through the opening of the foundation body into the hollow space of the cannula and thus into the tissue. In accordance with the invention, the plug can be attached to a contact point of the foundation body and tilted around the contact point such that the supplying element of the plug is guided into the opening of the foundation body. Connecting the plug of a liquid supply to the cannula in this way is advantageous since no exact positioning is required at the beginning of the connecting process, i.e., users who are restricted in their physical capacity, for example, can attach the plug to a contact point of the foundation body relatively easily, wherein the contact point need not be a point in the geometric sense but rather can also be formed as a contact edge having a linear or also curved or angled run, or as a contact area. If such a plug having a contact edge or a suitable protrusion of the plug is attached to a contact edge of the foundation body, which does not yet require great precision with respect to the contact position, then the plug can be gradually moved to the exact position by tilting around said contact edge, for example using suitable guides, such that the supply element can be inserted exactly into the opening of the foundation body when the plug is tilted completely down. Connecting a plug to the foundation body in this way is thus relatively fault-tolerant with respect to attaching the plug to the foundation body, and is greatly advantageous particularly when the cannula connected to the foundation body has been introduced using an inserting device already fixedly connected to the foundation body, as described above. In this case, once the cannula has been inserted, the inserting device for the cannula merely has to be detached from the foundation body by the user, which does not require an exact positioning process, such that the only positioning process which has to be performed by the user is the fault-tolerant attaching of the plug to the contact point of the foundation body, wherein the supplying element is moved positionally exactly to the opening of the foundation body, preferably via a suitable guide while tilting the plug.

In some preferred embodiments, at least one guiding element is provided on the foundation body and/or the plug, in order to guide the plug during the tilting process once it has been attached to the contact point or contact edge. For example, a channel tapering widthways can be provided as the guiding element, with which a protrusion engages such that during the tilting process, the protrusion is guided along the channel towards the narrower end, which enables the plug to be exactly positioned relative to the foundation body. Both the channel and the plug can be provided on the foundation body and/or on the plug. Furthermore, it is also conceivable to provide lateral guides on the plug and/or foundation body, which are funnel-shaped in order to position the plug relative to the foundation body as desired. In general, any arrangement is suitable which enables the plug attached to at least one contact point to be guided in a guiding process and thus to be exactly positioned when it is tilted down.

In some embodiments, the plug is preferably formed such that it can jam with the contact point or a contact edge of the foundation body. What is meant by jam in the sense of the invention is that the plug abuts a point or a number of points, edges or areas of the foundation body and a loose connection between the plug and the foundation body is thus created, which enables tilting or a rotational movement about this connection. Preferably, at least one degree of freedom in the movement of the plug relative to the foundation body is to be restricted, such that once the plug has been jammed into the foundation body, the plug is firstly positioned roughly with respect to the foundation body.

In one preferred embodiment, the plug can be connected, e.g., latched or locked, to the foundation body, wherein suitable grooves, latching projections or the like can be provided to this end. The connection or latch connection can be designed to be detachable or non-detachable.

In accordance with another aspect of the invention, a foundation body comprises a rotatably mounted swivel which is fixedly connected to the foundation body. The swivel has an opening, sealed by a sealing element, which enables a cannula including, for example, a needle, to be introduced in a first position of the swivel and enables a supplying element for supplying liquid to be introduced in a second rotated position. Providing a swivel on the foundation body incurs the advantage that if the opening of the swivel is aligned upwards, i.e., in a direction in which the opening lies on an extension of the desired position of the cannula to be inserted, the cannula can be inserted through the opening of the swivel and through the foundation body, directly into the tissue. Once the cannula has been inserted, and the inserting device of the cannula loosened as the case may be, the swivel can be rotated such that a supplying element for supplying liquid can be connected laterally or when the opening of the swivel is not pointing upwards. A cannula can thus be easily inserted and a liquid supply can be connected laterally, which keeps the overall height of the device low when the cannula is inserted and the liquid supply connected. The cannula can be connected to the opening of the swivel by a flexible tube element or other suitable device which enables a secure connection when the swivel is rotated.

In accordance with another aspect of the invention, a device for supplying a liquid into a tissue via a cannula comprises only one sealing element which serves to seal a liquid space and can be pierced by a cannula and/or a needle if the cannula is to be inserted into the tissue and can be penetrated by a supplying element if a liquid is to be supplied to the liquid space. In addition, other sealing elements can be provided.

In accordance with one aspect of the invention, a liquid can be supplied to a tissue via a cannula, wherein a cannula—in some instances, together with a needle—pierces a sealing element in order to insert the cannula into the tissue. If the cannula has been inserted, then a supplying element is inserted through the sealing element, once the needle has been removed as the case may be, in order to insert a liquid into the tissue via the supplying element, through the sealing element and the cannula.

In accordance with another aspect of the invention, a device for inserting a cannula into tissue is provided, wherein a cannula expelling device for expelling the cannula and inserting the cannula into tissue is provided. In accordance with the invention, a restoring element is coupled to the cannula expelling device in order to retract the cannula expelling device once the cannula has been expelled. In some embodiments, the restoring element is preferably a spring which can be biased such that the energy or force stored in the spring is sufficient to retract the cannula expelling device back from its expelled state, wherein completely retracting the cannula expelling device into its initial state is possible but not required. In accordance with the invention, the application of a cannula can thus be automated and therefore simplified by suitably selecting the parameters of the restoring element, such as a spring length and/or a spring constant, the restoring process of the cannula expelling device can be securely performed. That is, when these parameters are selected, a sufficient force is always available to securely retract the restoring element, without a user having to manually apply a large force.

In some embodiments, the cannula expelling device is preferably a guiding needle or other element bearing the cannula. A cannula without a guiding needle can thus for example be inserted by means of a suitable cannula holder.

In some preferred embodiments, a spring is provided as the restoring element, but other energy-storing or force-storing elements can also be used in accordance with the invention in order to retract the restoring element again, once the cannula has been inserted.

In some embodiments, a triggering element is preferably provided for the restoring element, wherein said triggering element can be operated manually or can be automatically triggered when the cannula inserting device is in a particular state. A push-button or other suitable switching or sliding element can be provided as a manual triggering element, which can release a safety catch of the restoring element. A holding element which locks the restoring element in the restoring direction can be provided as the safety catch, wherein said holding element is shifted when the safety catch is triggered—for example, when a push-button is pressed—such that a restoring force is applied to the cannula expelling device via the restoring element, in order to retract it. The holding element can be a laterally shifting element such as a pin or an edge, and can also be moved via a tipping or tilting mechanism.

Advantageously, the triggering element for the restoring element can be automatically triggered when the cannula inserting device is in a particular state. In some embodiments, a mechanism can be provided which automatically initiates the restoring process of the cannula expelling device when the cannula inserting device is removed from a foundation body. To this end, a cam can be provided on the foundation body, wherein said cam automatically operates a triggering mechanism for the restoring element when the cannula inserting device is removed from the foundation body.

An expelling element, for example a spring, can also advantageously be provided, which can generate a sufficient force for inserting the cannula into the tissue. The expelling element can be secured as described above for the restoring element and can likewise be triggered by a push-button. When both a restoring element and an expelling element are provided, a fully automatic cannula inserting device may be created, since a user does not have to actively apply a force, either to insert a cannula or to retract a cannula expelling device. Inserting a cannula, for example using a guiding needle, and retracting the guiding needle are thus fully automated, such that the danger of users incorrectly using the device is reduced.

The device for inserting a cannula into tissue can advantageously be designed such that a single energy-storing element, such as a spring or a number of co-operating energy-storing elements, is used to move a cannula expelling device or needle, preferably after having been suitably positioned, automatically i.e., without supplying external energy, such that the cannula is inserted into the tissue and the cannula expelling device is then automatically moved back, likewise without supplying an external force or energy, such that the cannula inserted into the tissue is removed, such that a user substantially does not have to apply any force, except to trigger the respective expelling and restoring processes.

In some embodiments, when using a single energy-storing device, such as a pressure spring, it is then advantageous to arrange the spring tensed in its initial state, i.e., before the cannula is inserted into tissue, such that when the spring is firstly partially relieved or partially expanded in a first direction, to expel the cannula expelling device or needle downwards from the cannula inserting device, the cannula expelling device is moved out of the cannula inserting device sufficiently far that the cannula or a cannula sub-assembly can be positioned on the tissue as desired, wherein when the spring is secondly partially expanded in a second direction, preferably opposite to the first direction, the cannula expelling device or needle is retracted again, such that the cannula or cannula sub-assembly can remain in the tissue and the cannula inserting device, preferably with the cannula expelling device or needle completely retracted, can be removed. Instead of a spring, which could be made of metal or plastic, other elements can also be used as the energy store, for example elements which store pressurized air or elements based on electrical, magnetic or other principles.

Preferably, a single triggering element is provided, such as for example a button, switch, tilting mechanism, sliding mechanism, latching mechanism, rotating mechanism, dial or lever, using which the expelling process and the restoring process of the cannula expelling device can be triggered, depending on its position. For example, a button can be provided in the form of an element which may be inserted or pressed and which for example is pressed along a first partial distance, once a safety-release process has been performed, in order to trigger the expelling process and is pressed in the same direction along a second partial distance having the same length or a different length, in order to trigger the restoring process. Alternatively, it is also possible for the one triggering element is operated in a first direction for triggering the expelling process and is moved in a second direction for triggering the restoring process of the cannula expelling device or needle, said second direction being different to said first direction, such as for example a movement in the opposite direction. Thus, using a single triggering element, such as for example a push-button, it is possible in succession to first insert the cannula into tissue using the cannula expelling device or needle by pressing the push-button, for example in a single direction, and then to restore the needle out of the inserted cannula or cannula sub-assembly, which enables the cannula inserting device to be operated very simply.

In general, a triggering element can also be formed as a rotating mechanism or a dial, wherein an expelling process can be triggered by rotating and a restoring process by rotating further in the same or alternatively in the opposite direction. Combinations of different triggering elements are also possible, in order for example to trigger an expelling process using a push-button or switch and a restoring process using a dial. Advantageously, a triggering element for restoring is only released once expelling is complete.

Advantageously, at least one securing element is provided on the cannula inserting device, said securing element preventing a triggering element from being unintentionally operated. Such a securing element may be designed such that it has to be removed from the cannula inserting device or moved to a safety-release position on the cannula inserting device, in order to be able to operate the triggering element at all. The securing element can be designed as a securing cap which at least partially and, preferably, approximately completely surrounds the triggering element and protects it from being unintentionally touched and thus from being undesirably triggered. Furthermore, the securing element can also be designed as a device for blocking or arresting the triggering element which has to be shifted first before in order to be able to operate the triggering element. It is then advantageous to design the securing element such that it cannot simply be moved by an unintentional touch or a jolt, but rather can only be moved by a pressing movement between two fingers to a position in which the triggering element can be operated. The securing element can then be designed such that it either requires a constant pressure or drag in order to move the triggering element to the safety-release position or remains in the safety-release position once a safety-release process has been performed and locks in, such that the triggering element can be operated once the safety has been released.

In some embodiments, the cannula inserting device can be designed as a disposable device in which the restoring element and/or expelling element are already biased in order to automatically insert the cannula and/or automatically restore the cannula expelling device. The cannula inserting device can, however, also be designed as a reusable cannula inserting device in which the restoring element and/or expelling element are formed such that they may be loaded or tensed. Thus, a mechanism can be provided for re-tensing a restoring spring and/or an expelling spring, after a cannula has been inserted and/or a cannula expelling device retracted, such that the cannula inserting device can be used to insert another cannula.

In general, the cannula inserting device can, in accordance with the invention, be designed to be fully automatic, i.e., both an expelling element for the cannula and a restoring element can be provided. Alternatively, it is also possible to provide only one of these two elements, in order to create a semi-automatic cannula inserting device, wherein the other process in each case then has to be performed manually. It is possible to only automate inserting the cannula, by providing an expelling element; retracting the cannula expelling device may then be performed manually.

Deviating from the exemplary latch connections described above, for connecting the respective devices to a foundation body all the described embodiments of an infusion set or cannula inserting device and/or a liquid supplying device can also comprise a rotational or screw connection which can be latched in one or more positions, such that the respective devices can be connected to and/or detached from each other by rotating, and the latch connections described may be omitted.

The devices described above in accordance with the individual aspects of the invention can be used both independently of each other and in combination with elements in accordance with other aspects of the invention.

DETAILED DESCRIPTION

Figure 1:
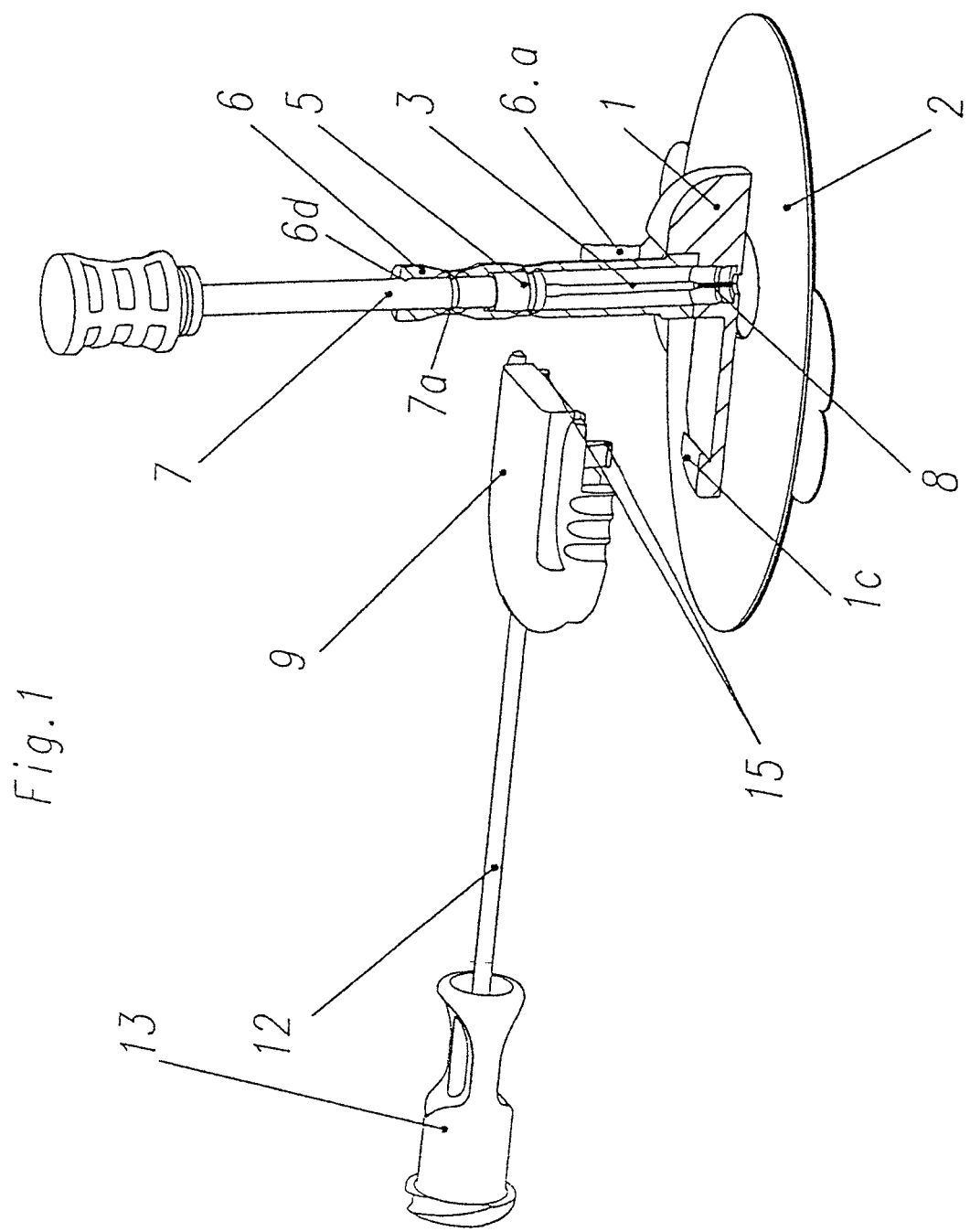
FIG. 1 depicts a first embodiment of an infusion set, in accordance with the invention, of a device for inserting the cannula, attached to a base body.

FIG. 1 shows an infusion set including a cannula inserting device 3-8, fixedly pre-assembled to the base body 1, 2. The base body 1, 2 consists of a foundation body 1 and a plaster 2 which exhibits an adhesive lower surface in order to be able to adhere the base body over an injection point. The foundation body 1 is arranged, e.g., adhered, on the upper side of the plaster 2 and is fixedly connected to the cannula inserting device 3-8 by the bracket 6a. The cannula inserting device comprises a guiding needle 8 which is guided through the cannula 3 and using which the cannula 3 can be inserted into a tissue from the underside of the foundation body 1. On the upper side of the cannula 3, i.e., the side of the cannula 3 facing away from the tip of the guiding needle 8, a holder 5 is fixedly connected to the cannula 3, wherein a sealing element or septum 4 is provided in the holder 5, as shown in FIG. 3. The guiding needle 8 and the cannula 3 are surrounded by the guiding element 6 which serves as a protective element, such that on one hand there is no danger of injury to a user since the tip of the guiding needle 8 does not protrude out of the arrangement shown and is still arranged within the foundation body 1 or guiding element 6, and, on the other hand, the arrangement shown in FIG. 1 largely prevents the guiding needle 8 and the cannula 3 from being contaminated before the cannula 3 is inserted into tissue. The later advantage is provided since direct contact between the cannula 3 and the guiding needle 8 and the environment is prevented by the guiding element 6 and the foundation body 1. The guiding needle 8 is fixedly connected to the operating element 7, as shown in FIG. 2, and can be expelled from the foundation body 1 by pressing downwards on the operating element 7, in order to insert the cannula 3 into a tissue.

Figure 2:
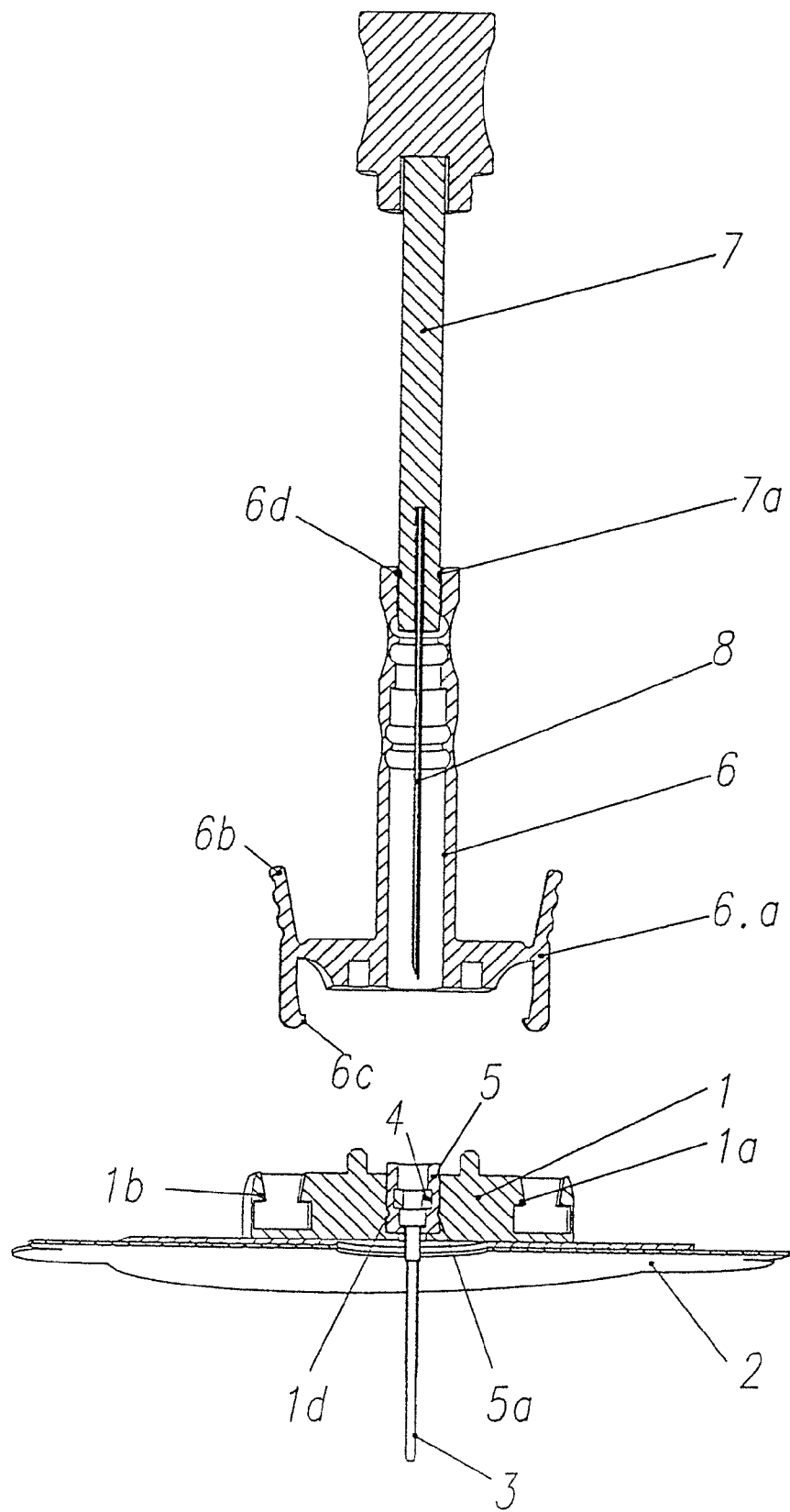
FIG. 2 depicts the device in accordance with FIG. 1, wherein the cannula inserting device has been loosened from the base body.
Figure 3:
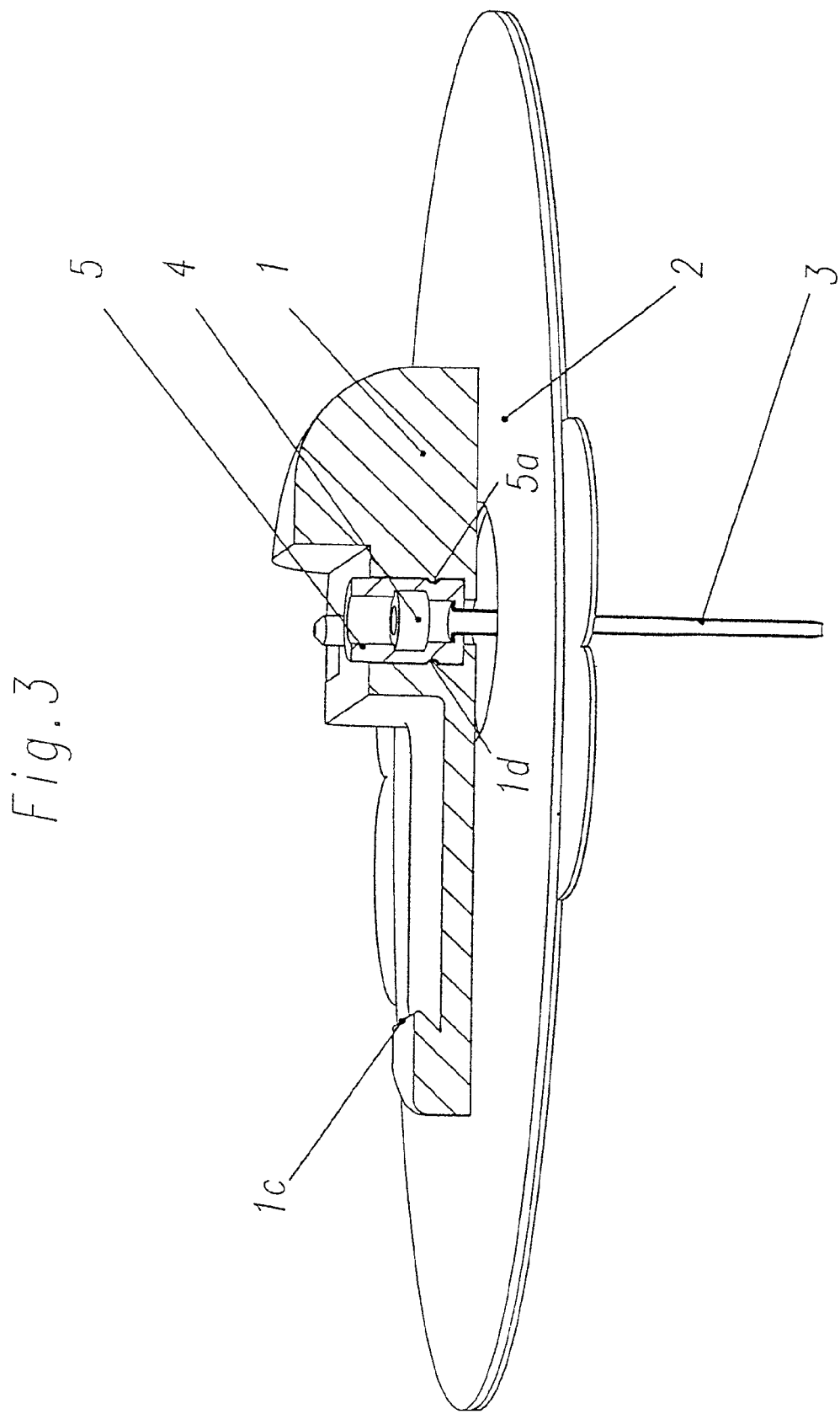
FIG. 3 is a partial sectional view of the base body, with a cannula inserted.

FIG. 2 shows the arrangement of FIG. 1, after the cannula 3 has been inserted and the connection between the cannula inserting device and the base body has been released. By pressing the operating element 7 downwards, the guiding needle 8 has been shifted downwardly together with the cannula 3 and the cannula 3 has been inserted into a tissue (not shown) below the plaster 2. This has inserted the holder 5 connected fixedly to the cannula 3, together with the sealing element 4 within it, into the foundation body 1 until an annular protrusion 1d of the foundation body 1 engages with a channel 5a running around the holder 5 and thus latches the holder 5 into the foundation body 1. Once the holder 5 has been latched in the foundation body 1, the guiding needle 8 can be removed from the cannula 3 by moving the operating element 7 upwards, without an excessively large force acting on the inserted cannula 3 during this process of removing the guiding needle 8 from the cannula 3. Latching the holder 5 into the foundation body 1 fixedly anchors the holder 5 in the foundation body 1 if an upward force relative to the guiding element 6, which is still connected to the foundation body 1 during the removing process, acts on the guiding needle 8, and thus enables the drag on the cannula 3 to be relieved during the needle 8 removing process.

The outer area of the holder 5, which is guided in the interior of the guiding element 6, can exhibit a surface structure or comprise one or more elements projecting outwards which enable the holder 5 to move in the expelling direction but prevent or hamper it from moving in the restoring direction, such that incorrect use may be prevented. Accordingly, corresponding structures or elements can be provided on the inner side of the guiding element 6, in order to enable movement only in a predetermined direction.

If the brackets 6a of the guiding element 6 are moved by pressing the operating elements 6b together, such that the latching projections 6c of the guiding element 6 no longer engage with the latching projections 1a of the foundation body 1, then the cannula inserting device can be detached from the foundation body 1. In its most extreme upper position, the operating element 7 is fixedly latched to a circumferential protrusion 6d of the guiding element 6 via a circumferential groove 7a in the lower region of the operating element 7 and thus ensures that, once the cannula inserting device has been disconnected, the guiding needle 8 can no longer be unintentionally expelled from the guiding element 6. In the basic pre-assembled state of the cannula inserting device on the foundation body 1, as may be seen from FIG. 1, the operating element 7 is retracted far enough into the guiding element 6 that the circumferential groove 7a of the operating element 7 is positioned below the circumferential protrusion 6d, such that the operating element 7 only latches to the guiding element 6 once the cannula 3 has been inserted. FIG. 3 shows a partial section of the inserted cannula 3, with the holder 5 latched in the foundation body 1, wherein a sealing element 4 is arranged in said holder 5.

Figure 4:
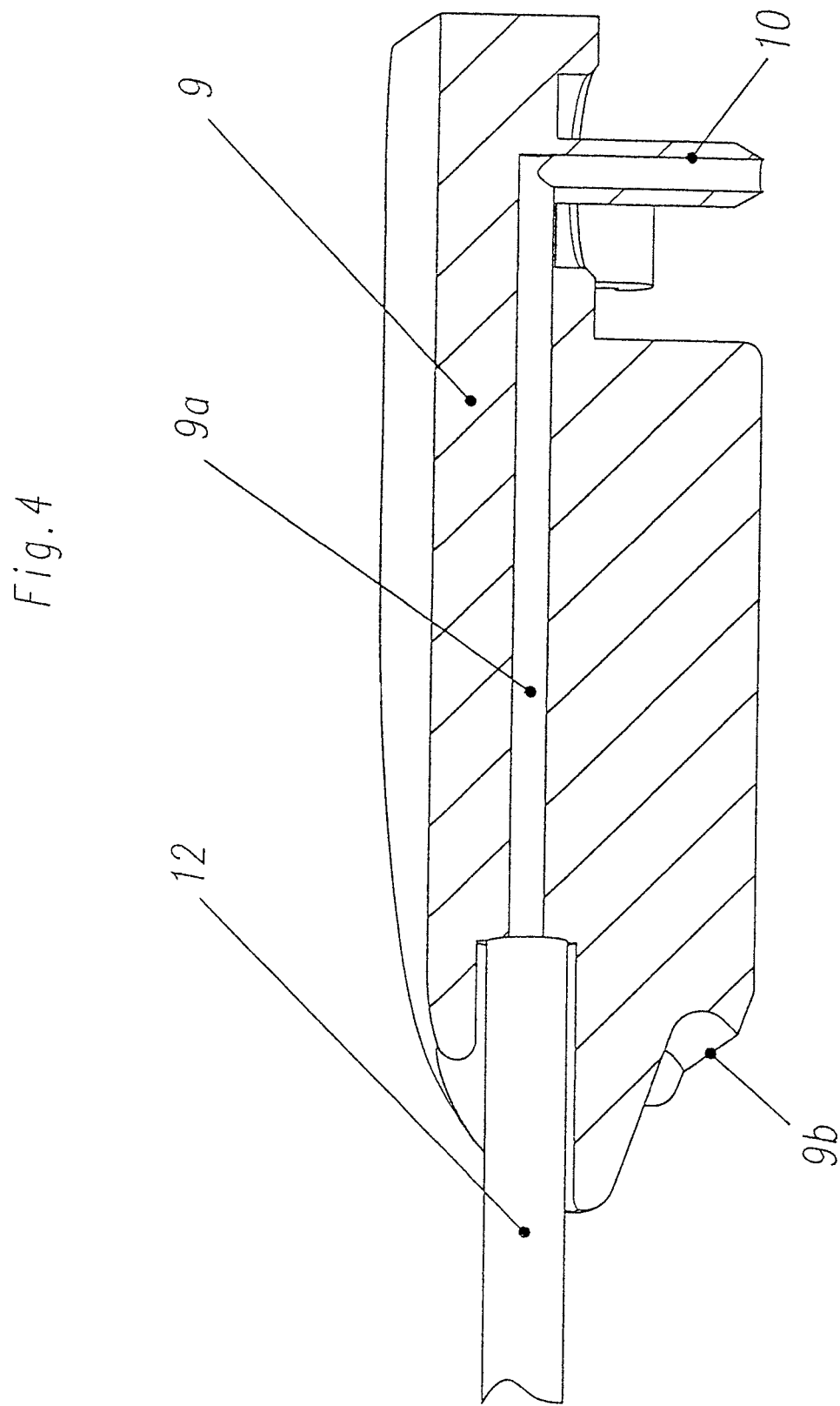
FIG. 4 is a cross-sectional view of a liquid supplying device.
Figure 5:
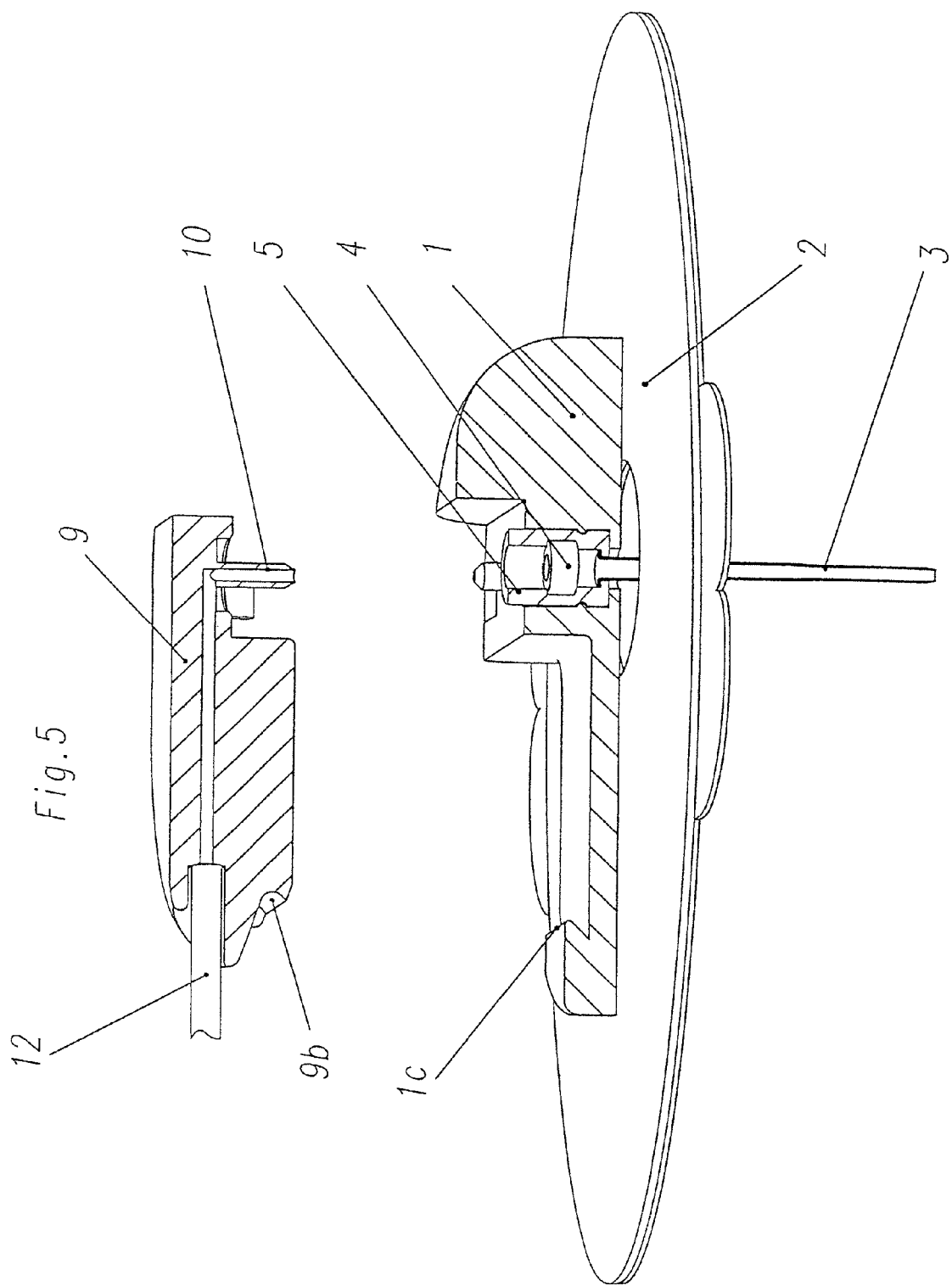
FIG. 5 is a partial cross-sectional view of the liquid supplying device to be inserted into the base body.
Figure 6:
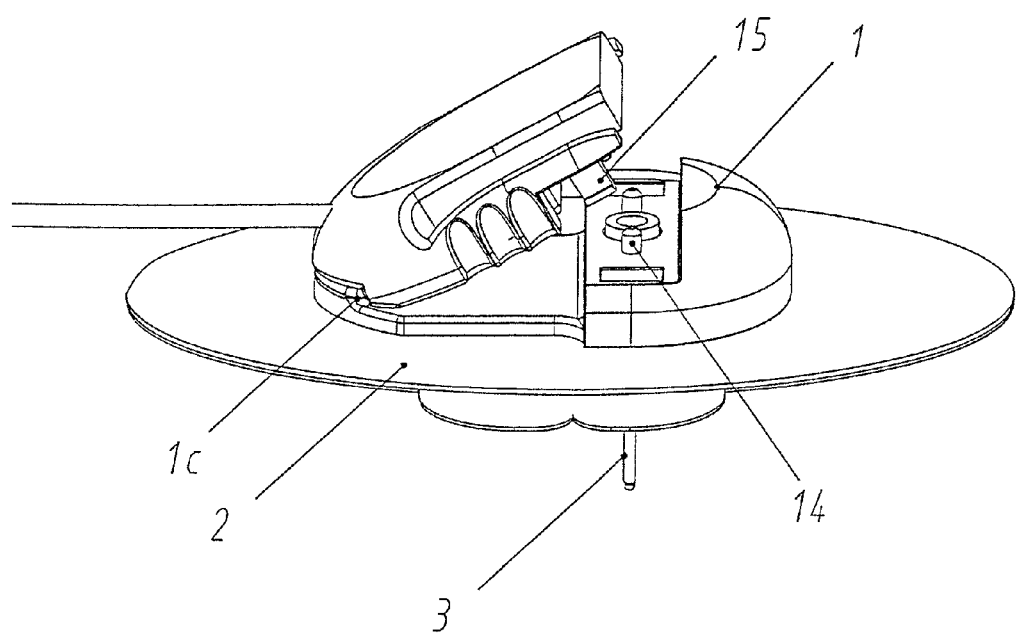
FIG. 6 depicts the arrangement in accordance with FIG. 5, with a plug of the liquid supplying device attached to the base body.

FIG. 4 shows a sectional image of the plug 9 of the liquid supply device shown in FIG. 1. The coupling part 13 of the tube 12 is connected to a liquid conveying means (not shown). The entire liquid space of the coupling part 13, the tube 12 and the plug 9 is then flooded. The plug comprises a plug cannula 10 which is connected to the tube 12 by the conduit 9a running through the plug 9. The plug 9 is moved to a position above the foundation body 1 as shown in FIG. 5 and brought into contact with the edge 1b of the foundation body 1 via the edge 9b running along the lower rear side of the plug 9. The plug 9 is preferably tipped slightly upwards for this, as shown in FIG. 6, such that the edge 9b protruding from the plug 9 is inserted into the gap defined by the upper side of the foundation body 1 and the jutting edge 1c of the foundation body 1. The plug 9 can thus be moved to a first contact position with the foundation body 1 in a relatively simple and user-friendly way. If the edge 9b of the plug 9 engages with the gap defined by the edge 1c of the foundation body 1, then the plug 9 can be tilted downwards about the point of rotation defined by this engagement, in order to introduce the plug cannula 10 into the casing 5 through the sealing element 4 and thus to enable a liquid to flow from the liquid conveying means through the coupling part 13, the tube 12, the plug 9 and the plug cannula 10 into the cannula 3 and thus into the surrounding tissue.

Figure 7:
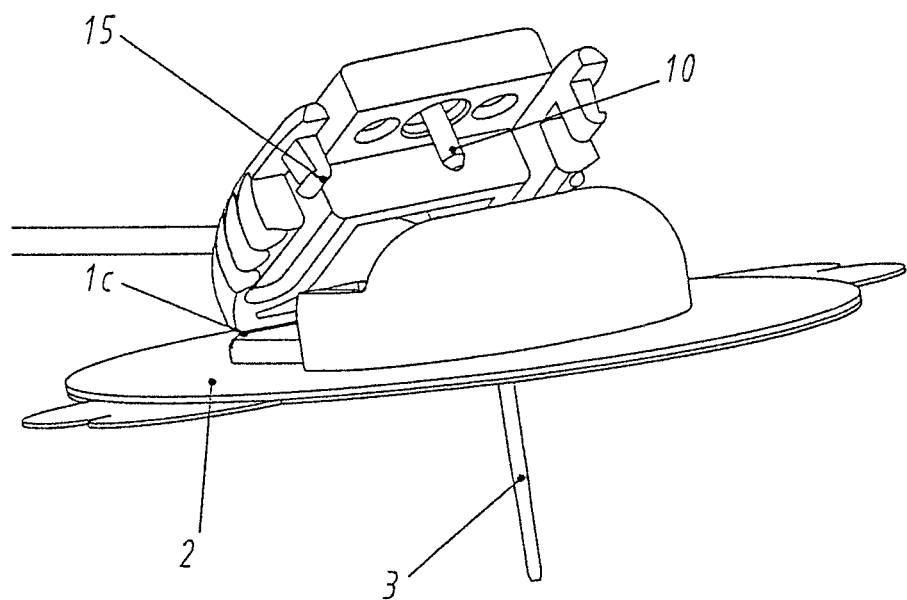
FIG. 7 depicts the arrangement of FIG. 6, from a different angle.

If the plug 9 is tilted downwards from the position shown in FIGS. 6 and 7, it is guided via guiding cams 14 in order to introduce the plug cannula 10 into the casing 5 positionally exactly. By guiding the plug 9 as it is tilted, by means of the guiding cams 14, it is possible to correct a lateral offset of the plug 9 relative to the foundation body 1 such as may arise as the plug 9 is attached to the edge 1b of the foundation body 1, such that the plug cannula 10 can always be securely introduced into the casing 5.

When the plug 9 is completely tilted down, the plug cannula 10 having been introduced into the casing 5, the latch devices 15 provided laterally on the plug 9 latch with the latching projections 1b of the foundation body 1, shown in FIG. 2, which connects the plug 9 securely to the foundation body 1.

Figure 8:
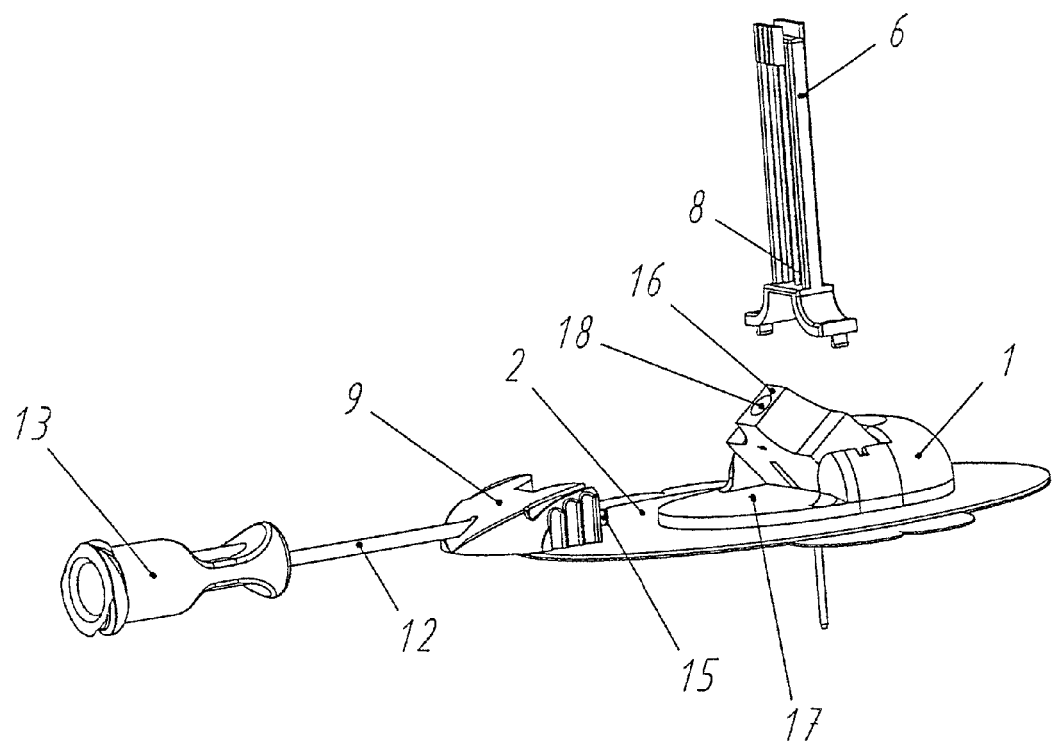
FIG. 8 depicts an alternative embodiment of the invention, comprising a dial.

FIG. 8 shows an alternative embodiment of the present invention. A swivel 16, rotationally mounted in the foundation body 1, can be moved to a position in which the opening 18 of the swivel 16 points upwards. In this position, a cannula can be inserted into the foundation body 1 with the aid of the guiding needle 8 which is protected by a frame serving as a protective element 6, as described above. Once the cannula has been inserted, the guiding needle 8 can be removed again. The swivel 16 can then be rotated on its side, as shown in FIG. 8, and preferably latches to a latching projection 17 pointing upwards and arranged on the base plane of the foundation body 1, which holds the swivel 16 securely in its tilted down position. In this alternative embodiment, a plug 9 can be attached laterally to the completely tilted down swivel 16, such that the plug cannula 10 running in the linear extension of the tube 12 can be inserted into the opening 18, pointing to the side, of the swivel 16. A latching device 15 attached to the plug 9 can then latch with suitable counter pieces of the swivel 16.

In each of the embodiments described above, the plug 9 can be disconnected again from the foundation body 1 by laterally pressing on the regions lying above or to the side of the latching devices 15 of the plug 9. Once the plug 9 has been disconnected, the sealing element 4 again completely closes access to the cannula 3.

Figure 9:
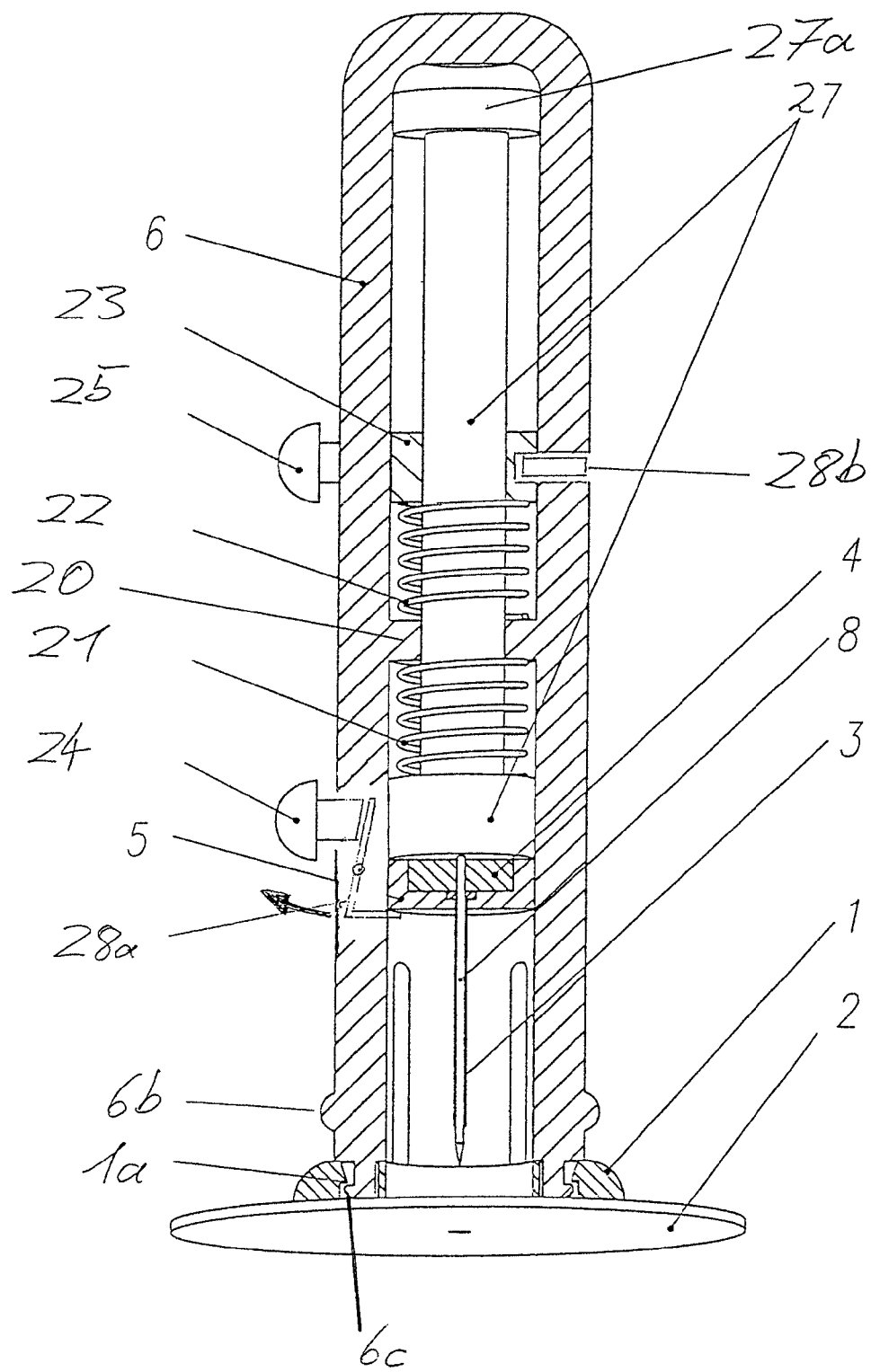
FIG. 9 depicts an embodiment of an automatic cannula inserting device, in its initial state.

FIG. 9 shows an automatic cannula inserting device in accordance with the invention. With respect to describing the foundation body 1, together with the corresponding latch connections, and inserting the cannula 3, together with its holder 5 and sealing element 4, reference is made to the description above. A needle carrier 27 which may be moved in the longitudinal direction of the guiding element 6 is provided in the guiding element 6, said needle carrier 27 being fixedly connected to the guiding needle 8. Alternatively, the guiding needle 8 can also be designed such that it can be coupled to the needle carrier 27, in order for example to be able to exchange the guiding needle 8. The needle carrier 27 is situated in a retracted position and is biased by an inserting spring 21 abutting the front side of the needle carrier 27, said inserting spring 21 being supported against a supporting element 20 provided roughly in the middle part of the guiding element 6 and biasing the needle carrier 27, which is secured by the holding element 28a, in the expelling direction of the cannula 3. The holding element 28a can be released by a first triggering button 24. On the opposite side of the supporting element 20, a restoring spring 22 is provided which presses against a holding ring 23 which is secured by a holding element 28b and can be released by a second triggering button 25. The needle carrier 27 runs in the longitudinal direction of the guiding element 6, through the two springs 21 and 22 and may be shifted through the supporting element 20 and the holding ring 23 and comprises a holding element 27a at its rear end in order to prevent it from being able to pass completely through the holding ring 23. If the triggering button 24 is pressed, then the schematically drawn holding element 28a is slid or tilted radially outwards in the direction of the arrow, the tilting mechanism preferably being formed completely within the guiding element 6, wherein the needle carrier 27 is then no longer held in the expelling direction of the cannula 3 and is accelerated downwards by the force of the inserting spring 21 in order to expel the cannula 3 from the guiding element 6 via the guiding needle 8 and to insert it through the plaster 2 into a tissue. The expelling movement is continued until the holding element 27a of the needle carrier 27 abuts the holding ring 23.

Figure 10:
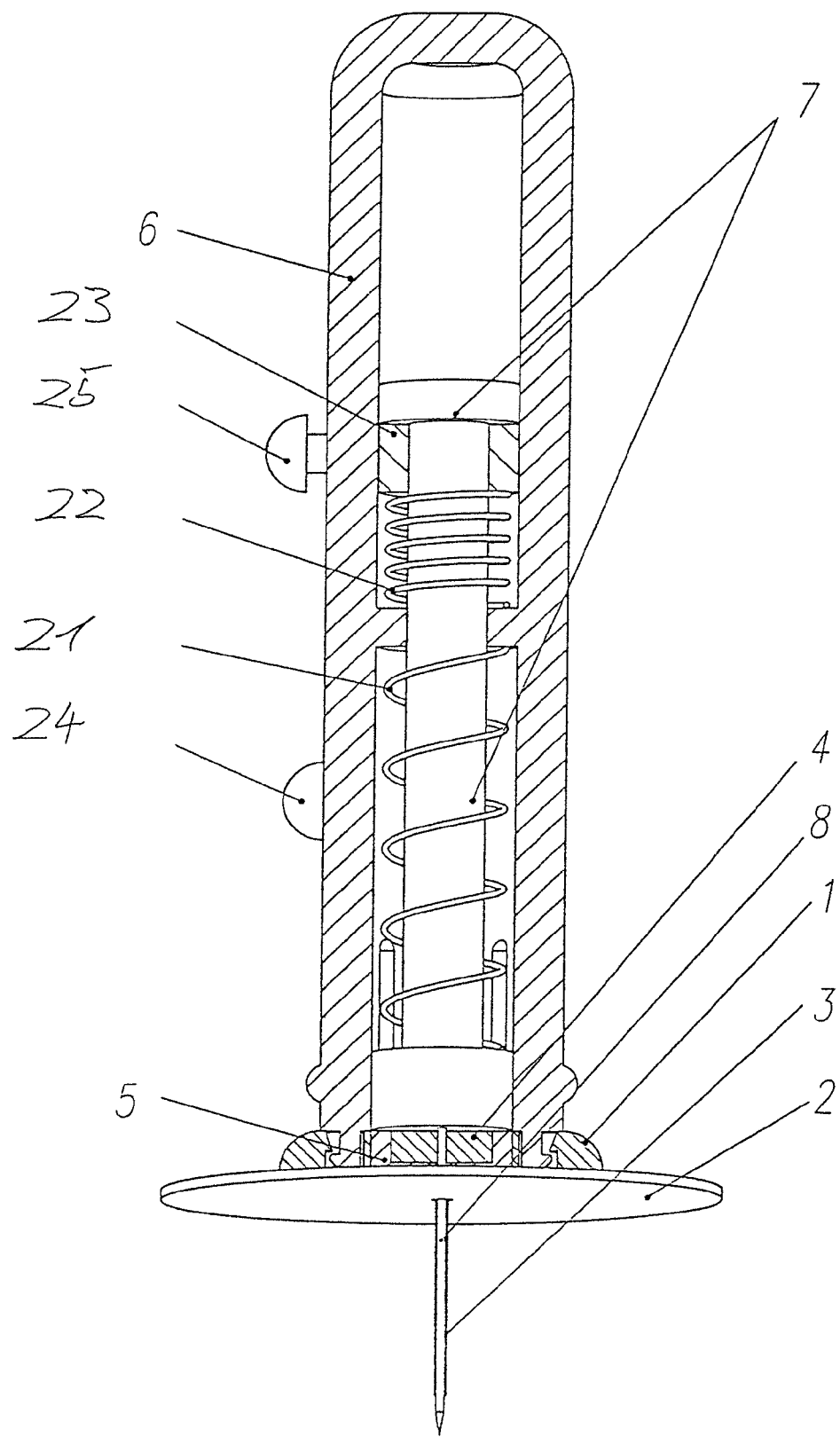
FIG. 10 depicts the cannula inserting device shown in FIG. 9, after the cannula has been inserted.

FIG. 10 shows the cannula inserting device shown in FIG. 9, once the process of expelling the cannula 3 has been completed. The inserting spring 21 has transferred the energy stored in it to the needle carrier 27 and is relieved. The holder 5 can, for example, be latched to the foundation body 1 as described above. If the second triggering button 25 is then operated by the user, the holding element 28b which may be radially shifted (FIG. 9) is pushed out of the holding ring 23 and the holding ring 23—which has so far been secured against moving axially in the guiding element 6—is released, such that the restoring spring 22 presses against the holding ring 23 and the holding element 27a of the needle carrier 27 and a restoring force thus acts on the needle carrier 27. In the embodiment shown, the restoring spring 22 is preferably designed such that it can apply a stronger force than the inserting spring 21, since the latter is pressed together again as the needle carrier 27 is retracted. Alternatively, the needle carrier 27 can also be formed such that, once the cannula 3 has been inserted, there is no longer a coupling between the lower side of the needle carrier 27 and the inserting spring 21, such that the inserting spring 21 no longer has to be tensed as the needle carrier 27 is retracted.

In general, the holding element 28a and/or the holding element 28b can be formed as a tipping or sliding mechanism or as any other securing mechanism.

Figure 11:
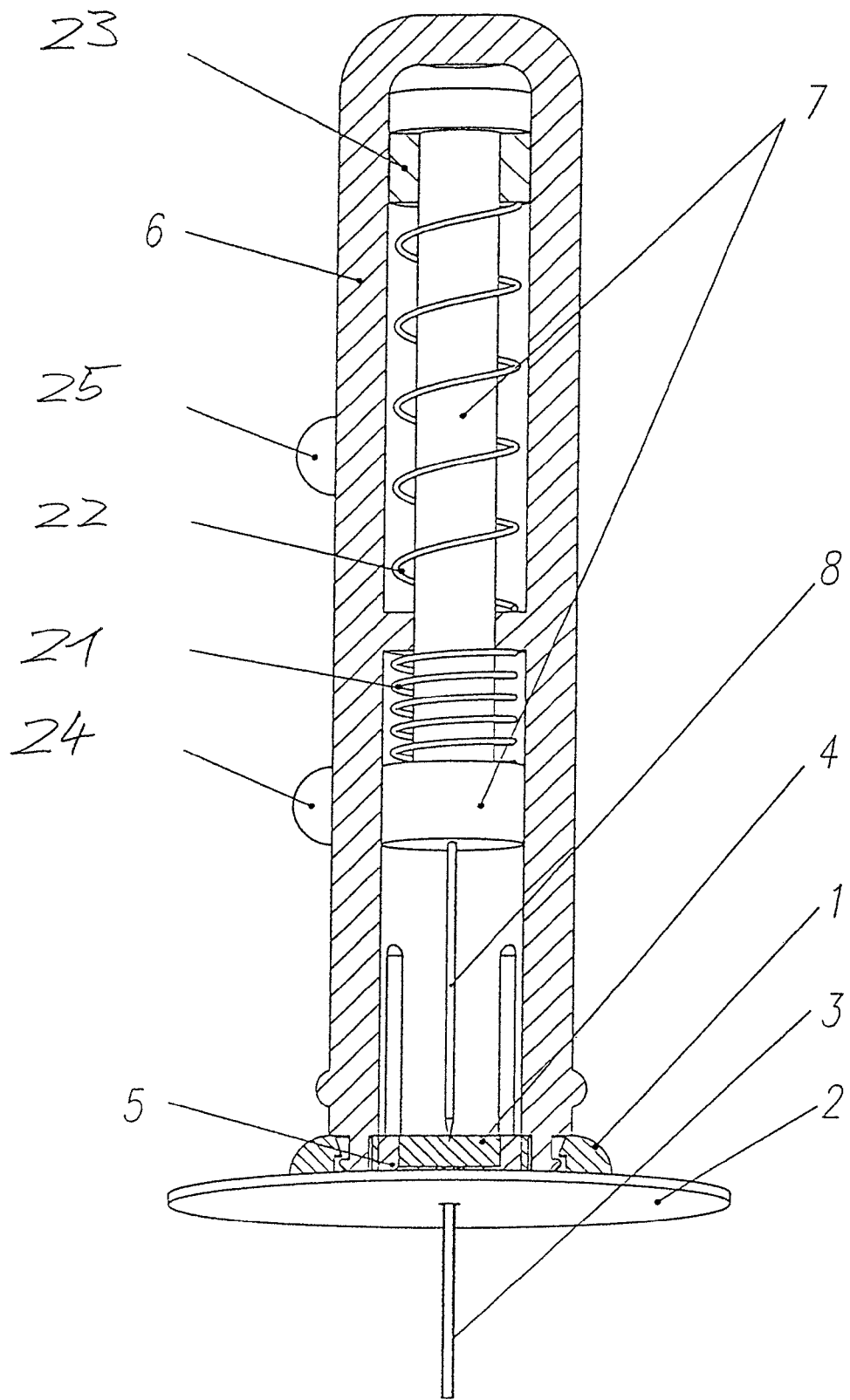
FIG. 11 depicts the cannula inserting device shown in FIG. 10, after the guiding needle has been restored.

FIG. 11 shows the cannula inserting device shown in FIG. 10, once the needle carrier 27 has been retracted. The guiding needle 8 has thus been retracted back out of the expelled cannula 3 and inserted back into the guiding element 6, in order to avoid injuries.

As an exemplary alternative to the embodiment shown, the needle carrier 27 can be retracted fully automatically, once the cannula 3 has been inserted, by operating a triggering mechanism for the restoring spring 22 via the underside of the needle carrier 27, which retracts the needle carrier 27 back immediately after the cannula 3 has been inserted. In this case, the second triggering button 25 can be omitted.

In accordance with another alternative embodiment, the restoring spring 22 can be triggered automatically by releasing the holding ring 23, when the cannula inserting device is removed from the foundation body 1, e.g., by simultaneously releasing the holding ring 23 when pressing in the buttons 6b in order to release the latch between the latching projections 6c of the guiding element 6 and the latching projections 1a of the foundation body 1.

The cannula inserting device is advantageously designed such that the latch between the guiding element 6 and the foundation body 1 cannot be released if the guiding needle 8 is in the position shown in FIG. 9 before the cannula 3 is expelled and/or in the expelled position shown in FIG. 10. This can be achieved if, for example, the underside of the needle carrier 27 is sufficiently wide that the underside of the guiding element 6 is prevented from being pressed together at the buttons 6b, and the latch between the guiding element 6 and the foundation body 1 cannot therefore be released in the position shown in FIG. 10.

Figure 12:
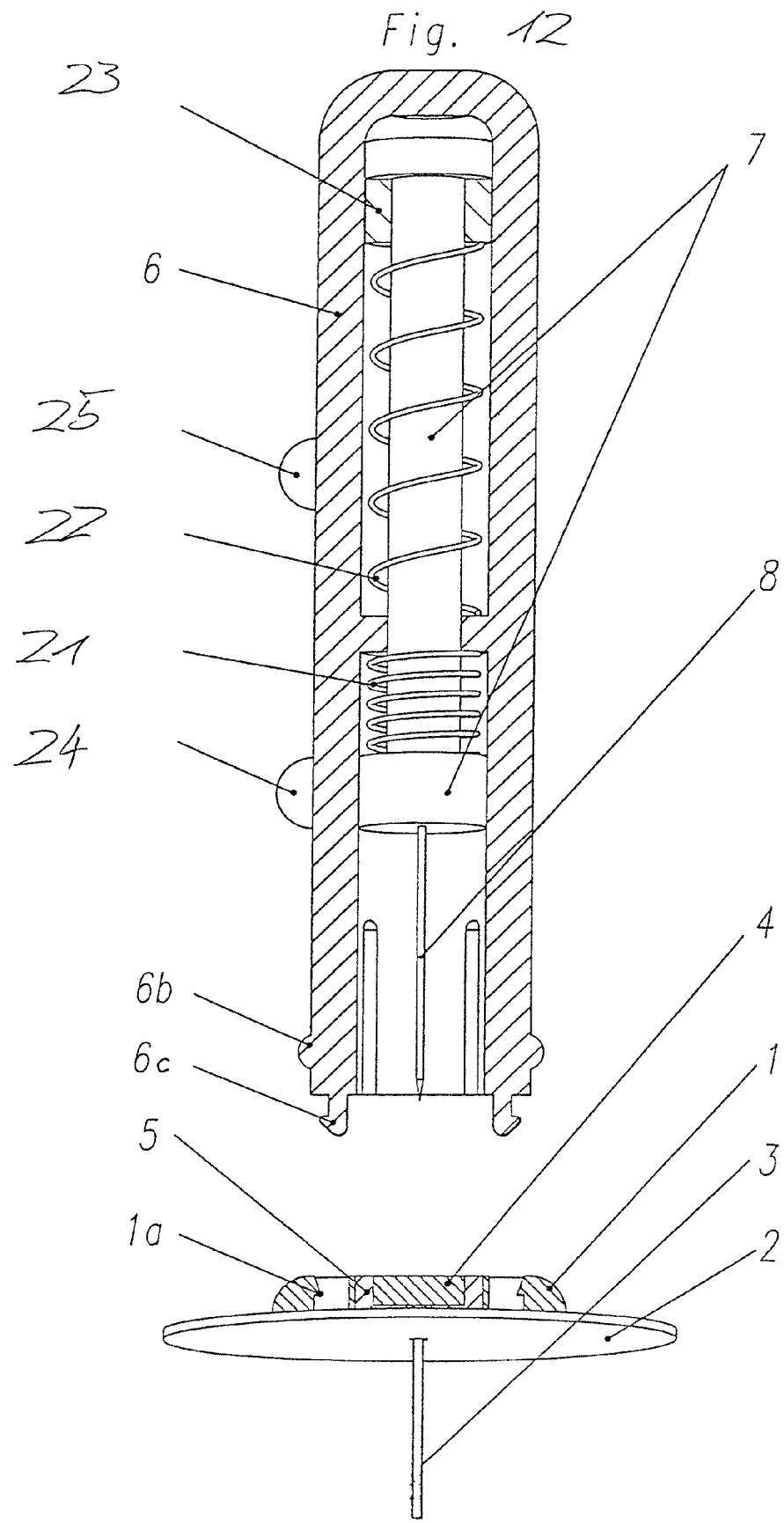
FIG. 12 depicts the cannula inserting device shown in FIG. 11, after having been separated from the foundation body.

FIG. 12 shows the cannula inserting device, detached from the foundation body 1, with the guiding needle 8 retracted. The cannula inserting device can now be safely disposed of, since the guiding needle 8 is covered by the surrounding guiding element 6 and the danger of unintentional pricking injury is minimized. Alternatively, the cannula inserting device can be moved back to the position shown in FIG. 9 using tensing devices (not shown), for example by pushing the holding ring 23 from its upper position back into a lower position, wherein the restoring spring 22 is re-tensed. It is equally possible to expel the needle carrier 27 from the guiding element 6 and thus tense the restoring spring 22, wherein the inserting spring 21 is then re-tensed in a second step. In the case of a reusable device, the used guiding needle is preferably exchanged and replaced with a new guiding needle, and a new cannula 3 and corresponding holder 5 including sealing element 4 as the case may be.

Figure 13:
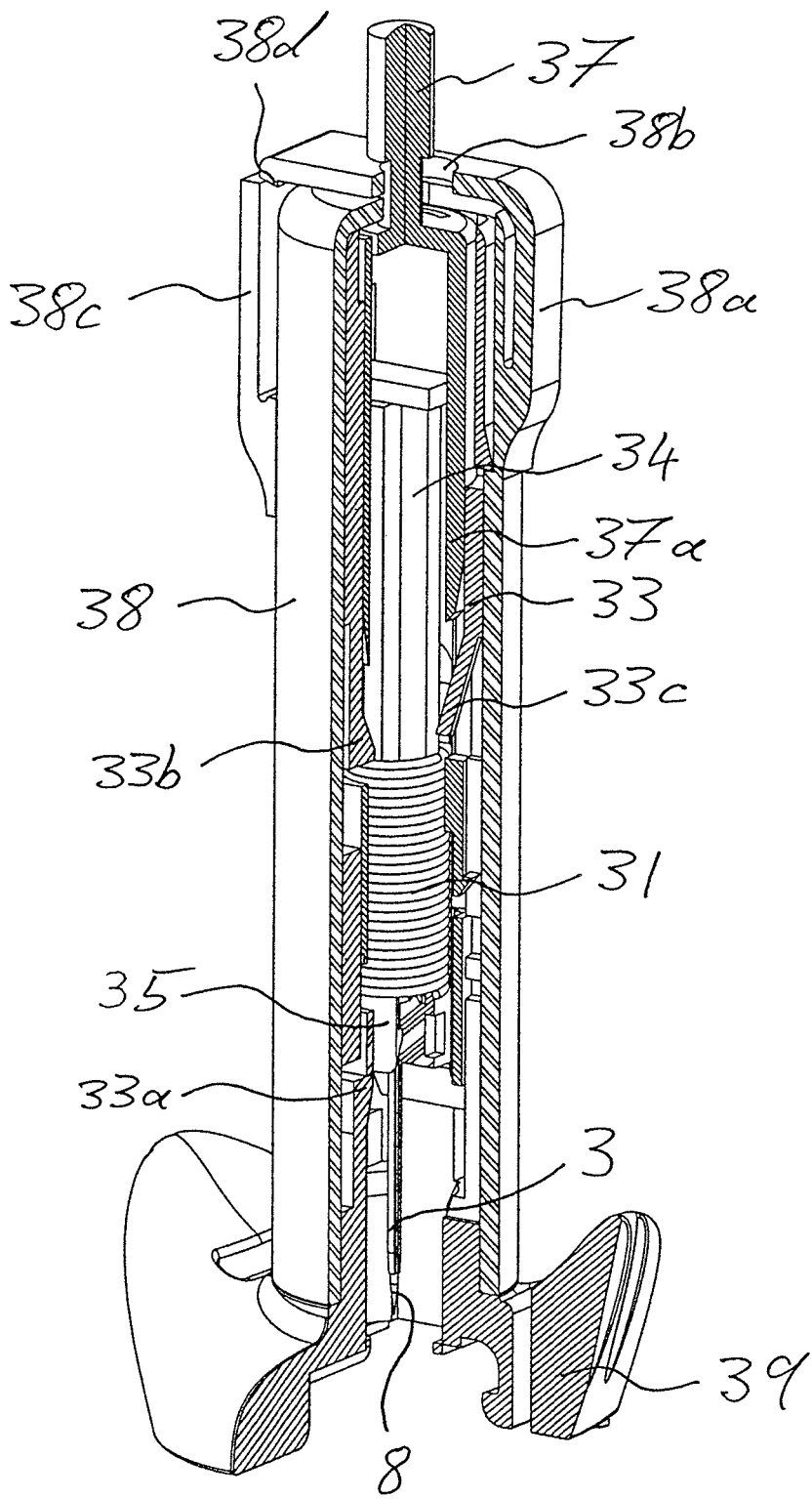
FIG. 13 depicts a first embodiment of an automatic cannula inserting and restoring device, in its initial state.

FIG. 13 shows a first embodiment of an automatic cannula inserting and restoring device, in its initial state before a cannula 3 on a cannula sub-assembly 35 has been inserted using a guiding needle 8. The cannula inserting device comprises a connector sleeve or guiding element 38 which has connector elements 39 at its lower end, in order for example to be fastened on a foundation or base body 1, as shown for one of the embodiments in the figures above. Said connector elements 39 for connecting the connector sleeve 38 to a predetermined base body comprise for example latching tongues 39a and other connecting elements (not shown). Within the connector sleeve 38, the guiding sleeve 33 is provided with tongues 33a, 33b and 33c protruding inwards from it. The tongues 33a to 33c are arranged at various positions in the axial direction of the guiding sleeve 33 and can be arranged as individual protruding elements or also over a large part of the circumference of the guiding sleeve 33. The tongues can also for example lie opposite each other and/or can be formed symmetrical with respect to each other as a number of individual tongue elements. The three tongues 33a to 33c shown by way of example are arranged offset with respect to each other in the axial direction of the guiding sleeve 33, in order to fulfill various functions when an expelling and restoring process is triggered, as will be explained below. A triggering sleeve 37a, fixedly connected to the triggering button 37, is provided within the guiding sleeve 33, said triggering sleeve 37a comprising indentations in the axial direction which are assigned to the tongues 33b and 33c. Furthermore, special triggering surfaces, such as chamfers, are provided on the triggering sleeve 37a in order to press away the tongues 33a to 33c in a predetermined order when the triggering sleeve 37a in the embodiment shown in FIG. 13 is shifted downwardly, initiating the expelling and restoring process of the cannula sub-assembly 35. Furthermore, a needle part or needle carrier 34 is arranged, such that it may be shifted, within the connector sleeve 38, and is coupled to the cannula sub-assembly 35 via a fixedly connected guiding needle 8 and a direct contact area or is latched to the cannula sub-assembly 35 via a suitable latching device (not shown). In the initial state shown, the completely biased spring 31 presses on the cannula sub-assembly 35, wherein a pair of tongues 33b arranged symmetrically above the spring 31 and a pair of tongues 33a of the guiding sleeve 33 arranged below the cannula sub-assembly 35 hold the biased spring 31 pressing on the cannula sub-assembly 35 in position. A securing clip 38a with a bore 38b is provided on the upper side of the connector sleeve 38, wherein the diameter of the bore 38b roughly corresponds to the diameter of the triggering button 37 and is preferably a little larger in order to enable the triggering button 37 to pass easily through. The approximately L-shaped securing clip 38a lies opposite a securing clip 38c comprising an elastic element on the upper side of the connector sleeve 38, wherein a tongue 38d provided on the securing clip 38a can latch with the securing clip 38c when the securing clip 38a and the securing clip 38c are pressed together. The bore 38b shown in FIG. 13, arranged eccentrically with respect to the cannula axis, prevents the triggering button 37 from being pressed. If the securing clip 38a and the securing clip 38c are pressed together such that the securing clip 38c locks in for example with the tongue 38d, then the bore 38b is moved to a concentric position with respect to the position of the triggering button 37, such that the triggering button 37 can be pressed.

Figure 14:
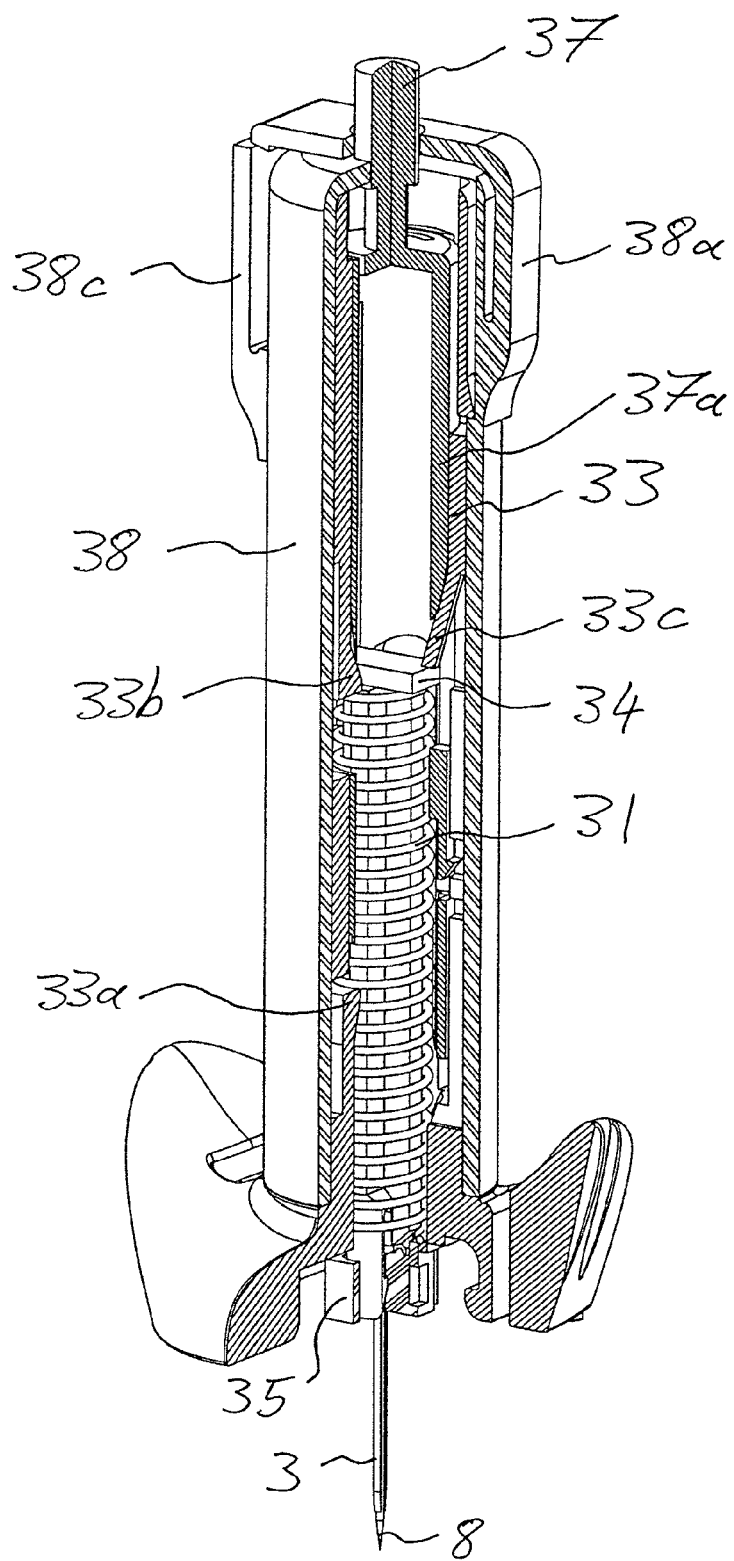
FIG. 14 depicts the device of FIG. 13, after the cannula has been inserted.

FIG. 14 shows the device shown in FIG. 13 once the operating button 37 has been pressed in by about a half length. The lower tongues 33a, which the cannula sub-assembly 35 has been pressed onto by the spring 31, are deformed by the triggering sleeve 37a extending along the inner side of the connector sleeve 38, which releases the cannula sub-assembly 35 together with the needle carrier 34, the spring 31 pressing on a lower end stopper which can be provided in the cannula inserting device or on a base body 1. The upper end of the needle carrier 34 thus leads over the tongues 33c. The cannula 3 of the cannula sub-assembly 35, connected to the guiding needle 8, is expelled downwards, out of the device, by the force of the spring 31, preferably at high speed, and can be inserted into a tissue as desired.

In the position shown in FIG. 14, the cannula sub-assembly 35 is latched to a foundation body or base body of an infusion set (not shown) and the needle carrier 34 is unlatched by tongues in the foundation body of the infusion set, such that the needle carrier 34 and the cannula sub-assembly are no longer connected (not shown in FIG. 14). In this position, the needle carrier 34 is latched by the two tongues 33c, arranged symmetrically with respect to each other, which makes it possible to re-position the set.

The semi-relieved spring 31 presses downwards against the expelled cannula sub-assembly 35 and abuts a protruding element of the needle part 34 on the opposite side, the needle part 34 being secured against shifting axially by the tongues 33c. In the position shown, the spring 31 is held by the tongues 33b. In general, the spring can also be held in the position shown for example by the upper end of the needle part 34.

Figure 15:
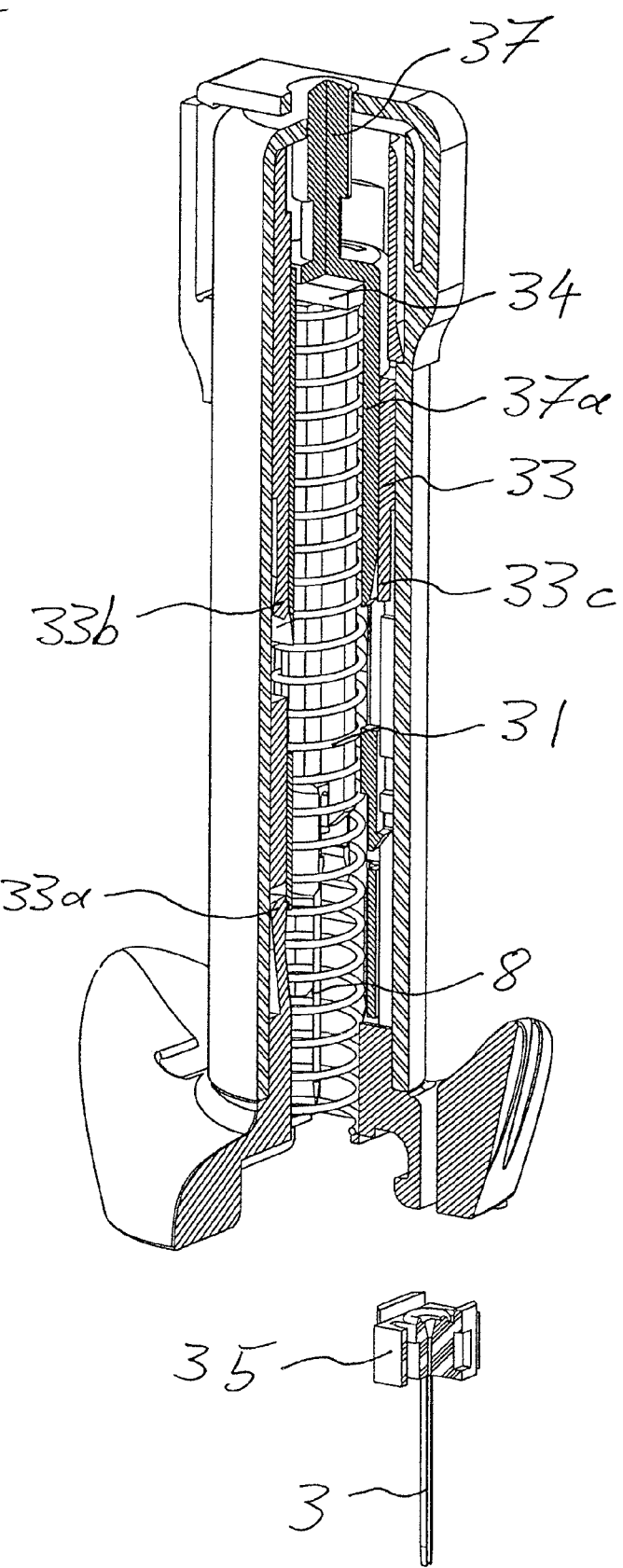
FIG. 15 depicts the device shown in FIG. 14, after the guiding needle has been restored.

FIG. 15 shows the device from FIG. 14 once the operating button 37 has been completely pressed in. This pushes the triggering sleeve 37a over the tongues 33b and 33c, which are pressed outwards and away and thus release the needle part 34 which is pushed back into the connector sleeve 38 again by the spring 31 which can now be fully relieved. This retracts the guiding needle 8 connected to the needle part 34 out of the cannula and the cannula sub-assembly 35 into the connector sleeve 38, wherein the cannula 3 can remain in a tissue. The needle part 34 is held in the retracted position by the spring 31, such that the guiding needle 8 cannot unintentionally exit the connector sleeve 38, which minimizes the risk of injury. The connector sleeve 38 can then be removed from a base body by detaching the connector elements 39.

Figure 16:
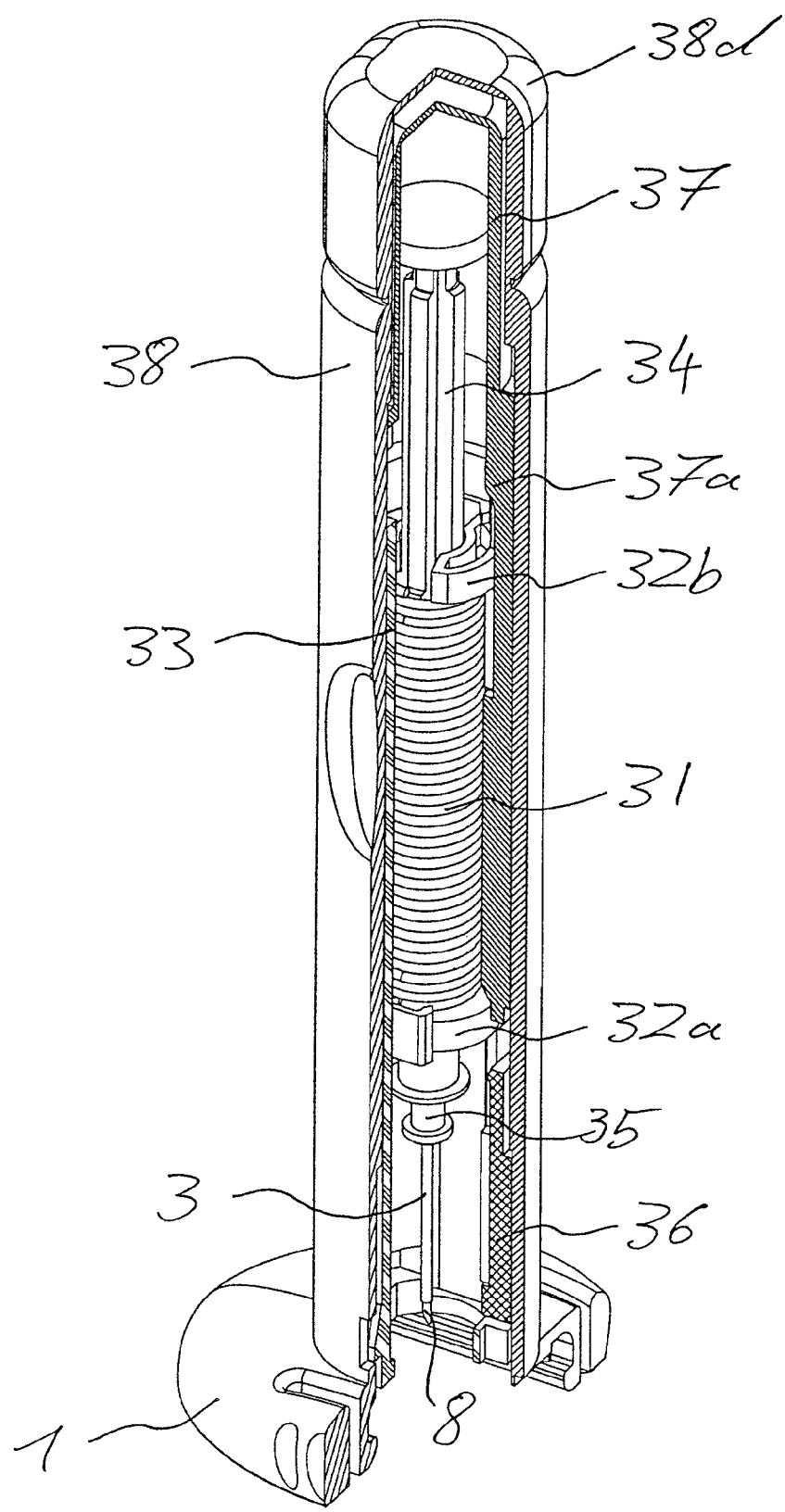
FIG. 16 depicts a second embodiment of an automatic cannula inserting and restoring device, in its initial state.

FIG. 16 shows a second embodiment of an automatic cannula inserting and restoring device in its initial state, comprising a connector sleeve 38 which is connected to a foundation body 1. A triggering button 37 passes into the triggering sleeve 37a arranged within the connector sleeve 38. The triggering sleeve 37a recesses and lower and upper chamfers on the inner side along its axial direction, using which a lower and an upper slaving ring 32a and 32b can be uncoupled when the triggering sleeve 37a is shifted axially, in order to expel the guiding needle 8, together with the cannula 3 arranged around it and the corresponding cannula sub-assembly 35, out of the connector sleeve 38 and to then retract the guiding needle 8 out of the cannula 3 and the cannula sub-assembly 35, as will be described below.

The lower slaving ring 32a abuts a stopper sleeve 36 and is held in position by the stopper sleeve 36 against the pressure of the spring 31. The spring 31 presses on the upper side against the upper slaving ring 32b which is held in position, for example in a channel or recess, by the guiding sleeve 33. The needle carrier 34 is designed such that it can be moved in the axial direction of the connector sleeve 38, through the slaving rings 32a and 32b, up to the end of the needle carrier 34 which exhibits a larger diameter than the inner diameter of the slaving rings in order for example to prevent the needle carrier 34 from falling out. The needle carrier 34 is in turn fixedly connected to the guiding needle 8.

Figure 17:
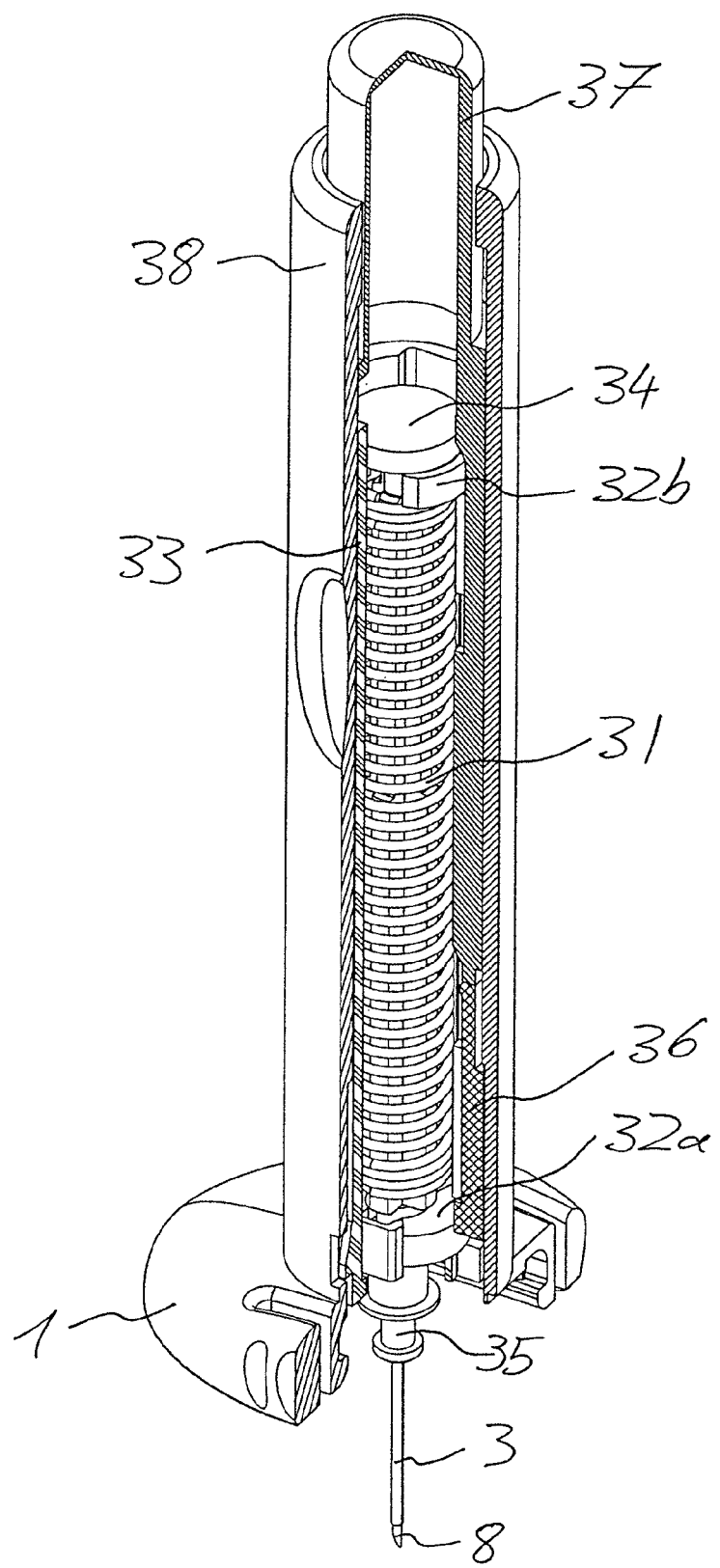
FIG. 17 depicts the device shown in FIG. 16, after the cannula has been inserted.

FIG. 17 shows the device shown in FIG. 16 once the securing cap arranged over the triggering button 37 has been removed and the triggering button 37 has been pressed in by about a half length. The lower slaving ring 32a is laterally shifted away from the stopper sleeve 36 by a lower oblique inner surface of the triggering sleeve 37a and thus uncoupled from the stopper sleeve 36. The lower slaving ring 32a can either already be coupled to the needle carrier 34 or can be coupled to the needle carrier 34 by this shifting process. The spring 31 then presses against the upper slaving ring 32b which is still held fixedly by the guiding sleeve 33 and presses the lower slaving ring 32a coupled to the needle carrier 34 downwards and thus inserts the guiding needle 8, together with the cannula 3, into a tissue lying below the foundation body 1, wherein the cannula sub-assembly 35 is in turn moved as far as a lower end stopper. In this position, the needle carrier 34 remains latched to the foundation body 1, which makes it possible to re-position the entire set.

Figure 18:
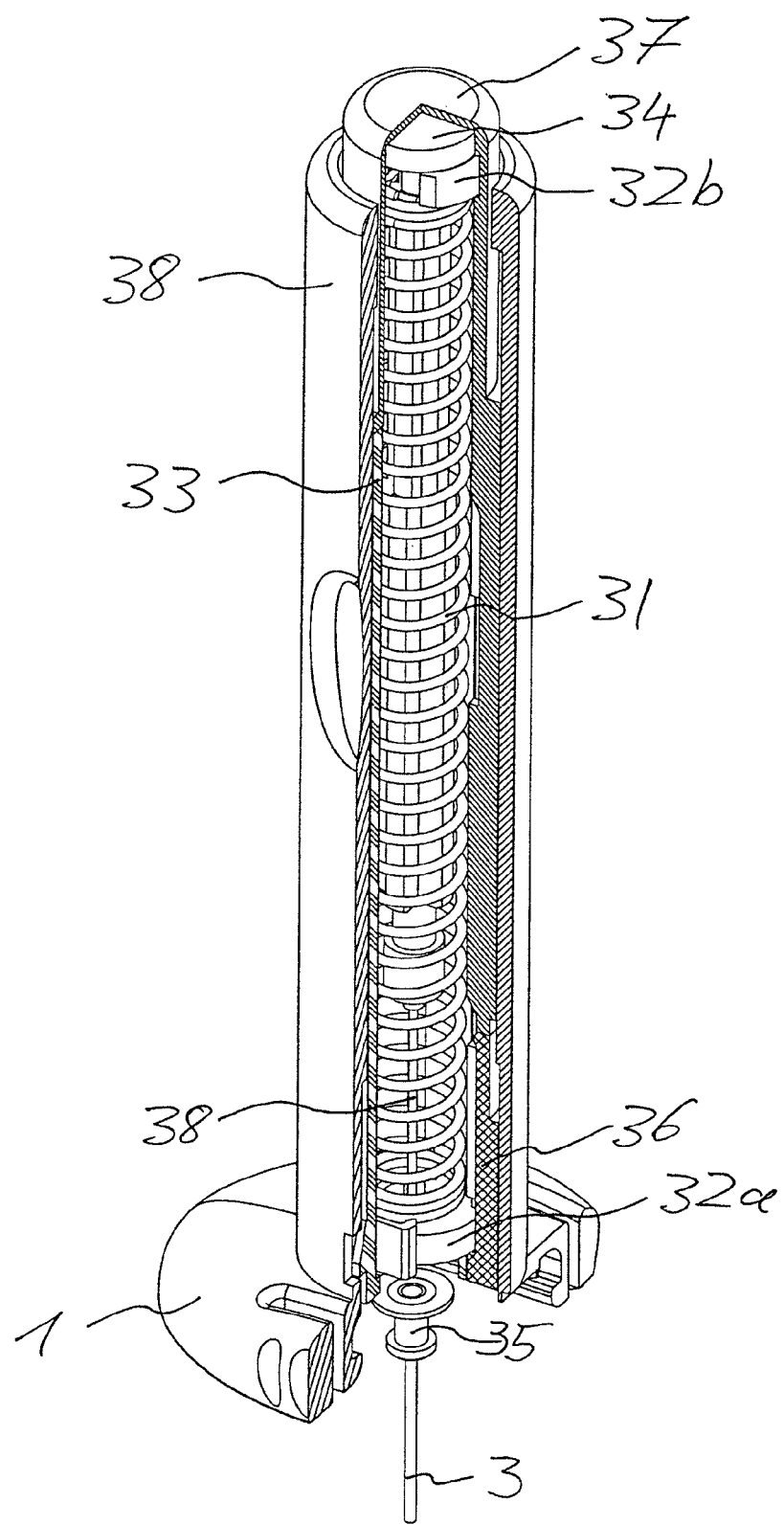
FIG. 18 depicts the device shown in FIG. 17, after the guiding needle has been restored.

FIG. 18 shows the device shown in FIG. 17 once the triggering button 37 has been pressed in further. This firstly unlatches the needle carrier 34 completely from the cannula sub-assembly 35. The upper slaving ring 32b is laterally shifted by an upper oblique area of the triggering sleeve 37a and thus uncoupled from the guiding sleeve 33 and couples into the needle carrier 34, such that the spring 31 can press the needle carrier 34 upwards via the upper slaving ring 32b, as far as an upper end stopper. This retracts the guiding needle 8 out of the cannula 3 and the cannula sub-assembly 35, which is held in the retracted position by the spring 31 pressing against the needle carrier 34, which minimizes the risk of injury. In general, one or more operating elements, e.g., buttons, can be provided for triggering the expelling and restoring processes, wherein said operating elements trigger, e.g., by releasing a spring, the corresponding process directly or indirectly, e.g., by shifting an element in the cannula inserting device.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:
1. A fluid delivery system, comprising:
a liquid supply;
a base body, the base body comprising a foundation body and a plaster, the foundation body attached to a first surface of the plaster, the plaster having a second, opposite surface comprising an adhesive for attachment of the base body to a tissue; and
a separate cannula holder comprising a cannula for delivering a fluid from the liquid supply, wherein the cannula holder and the foundation body are configured to form a connection as the cannula is inserted through the base body and into the tissue.

2. The system of claim 1, wherein the liquid supply is connectable to the foundation body with a latch connection.

3. The system of claim 1, wherein the liquid supply is connectable to the foundation body by a rotational connection.

4. The system of claim 1, wherein liquid supply is detachably connectable to the foundation body.

5. The system of claim 1, wherein the separate cannula holder further comprises a sealing element.

6. The system of claim 5, wherein the sealing element comprises a septum.

7. The system of claim 1, wherein the cannula holder connects to the foundation body by a latch connection.

8. The system of claim 7, wherein the latch connection comprises one or more of a groove, a recess, a projection or a latching edge on the cannula holder that connects to a corresponding structure on the foundation body.

9. The system of claim 7, wherein the latch connection comprises a groove on the cannula holder and a corresponding protrusion on the foundation body.

10. The system of claim 1, wherein the cannula comprises a hard cannula.

11. The system of claim 10, wherein the hard cannula becomes flexible once inserted into the tissue.

12. The system of claim 1 further comprising an inserting device.

13. The system of claim 12, wherein the foundation body comprises at least one connecting element.

14. The system of claim 13, wherein both the liquid supply and the inserting device connect to the same at least one connecting element.

15. The system of claim 13, wherein the connecting element is a detachable connecting element.

16. The system of claim 1, wherein the separate cannula holder further comprises a sealing element and the liquid supply comprises a supplying element that pierces the sealing element and channels a liquid from the liquid supply into a hollow space of the cannula.

17. The system of claim 1, wherein the foundation body has at least one opening connected to a hollow space of the cannula and the liquid supply comprises a supplying element that is inserted into the opening of the foundation body such that a liquid can be channeled via the supplying element into the hollow space of the cannula and into the tissue.

18. The system of claim 17, further comprising a sealing element arranged over the at least one opening that is pierced by the supplying element when the liquid supply is connected to the foundation body.

19. The system of claim 18, wherein the sealing element comprises a septum.

20. A fluid delivery system, comprising:
a liquid supply;
a base body, the base body comprising a foundation body and a plaster, the foundation body attached to a first surface of the plaster, the plaster having a second, opposite surface comprising an adhesive for attachment of the base body to a tissue;
a separate cannula holder comprising a sealing element and a cannula for delivering a fluid from the liquid supply, wherein the cannula holder and the foundation body are configured to form a connection as the cannula is inserted through the base body and into the tissue; and
an inserting device;
wherein the liquid supply comprises a supplying element that pierces the sealing element and channels a liquid from the liquid supply into a hollow space of the cannula.

21. The system of claim 20, wherein the liquid supply is connectable to the foundation body with a latch connection.

22. The system of claim 20, wherein the liquid supply is connectable to the foundation body by a rotational connection.

23. The system of claim 20, wherein liquid supply is detachably connectable to the foundation body.

* * * * *